(12) United States Patent
Yukawa et al.

(10) Patent No.: US 8,846,367 B2
(45) Date of Patent: Sep. 30, 2014

(54) CORYNEFORM BACTERIUM TRANSFORMANT AND PROCESS FOR PRODUCING PHENOL USING THE SAME

(75) Inventors: Hideaki Yukawa, Kyoto (JP); Masayuki Inui, Kyoto (JP)

(73) Assignee: Green Phenol Development Co., Ltd.

( * ) Notice: Subject to any disclaimer, the term of this patent is extended or adjusted under 35 U.S.C. 154(b) by 0 days.

(21) Appl. No.: 13/988,107

(22) PCT Filed: Nov. 17, 2011

(86) PCT No.: PCT/JP2011/076484
§ 371 (c)(1),
(2), (4) Date: Jun. 28, 2013

(87) PCT Pub. No.: WO2012/067174
PCT Pub. Date: May 24, 2012

(65) Prior Publication Data
US 2013/0267000 A1    Oct. 10, 2013

(30) Foreign Application Priority Data
Nov. 18, 2010    (JP) ................................. 2010-258089

(51) Int. Cl.
| | | |
|---|---|---|
| C12N 9/90 | (2006.01) | |
| C12N 1/20 | (2006.01) | |
| C12P 19/30 | (2006.01) | |
| C12P 7/22 | (2006.01) | |
| C12N 9/88 | (2006.01) | |
| C12N 15/77 | (2006.01) | |

(52) U.S. Cl.
CPC . *C12N 15/77* (2013.01); *C12P 7/22* (2013.01); *C12Y 401/99002* (2013.01); *C12N 9/88* (2013.01)
USPC ........................... 435/233; 435/89; 435/252.3

(58) Field of Classification Search
USPC ......................... 435/252.3, 89, 233
See application file for complete search history.

(56) References Cited

U.S. PATENT DOCUMENTS

| | | | |
|---|---|---|---|
| 5,185,262 A * | 2/1993 | Kohama et al. ............ | 435/320.1 |
| 2006/0275874 A1 | 12/2006 | Matsuno et al. | |
| 2007/0122888 A1 | 5/2007 | Boy et al. | |
| 2009/0258400 A1 | 10/2009 | Kumagai et al. | |
| 2011/0117612 A1 | 5/2011 | Yukawa et al. | |

FOREIGN PATENT DOCUMENTS

| | | |
|---|---|---|
| EP | 0394479 A1 | 10/1990 |
| EP | 2287287 A1 | 2/2011 |
| JP | 03-240492 | 10/1991 |
| JP | 04-218380 | 8/1992 |
| JP | 08-154675 | 6/1996 |
| JP | 2005278453 A | 10/2005 |
| JP | 2005333885 A | 12/2005 |
| JP | 2006320238 A | 11/2006 |
| JP | 2007117078 A | 5/2007 |
| JP | 2007514430 A | 6/2007 |
| WO | WO-9004031 A1 | 4/1990 |
| WO | WO-2009154122 A1 | 12/2009 |

OTHER PUBLICATIONS

International Search Report in corresponding PCT/JP2011/076484 mailed Jan. 17, 2012.
Written Opinion in corresponding PCT/JP2011/076484 mailed Jan. 17, 2012.
GenBank Accession No. AE017226, Mar. 2010.
GenBank Accession No. NC011830, Apr. 2010.
GenBank Accession No. CP000909, Dec. 2007.
GenBank Accession No. CP001037, Apr. 2008.
Wierckx et al., "Engineering of Solvent-Tolerant Pseudomonas putida S12 for Bioproduction of Phenol from Glucose," *Appl. Environ. Microbiol.*, 71(12): 8221-8227 (2005).
Smith et al., "The tpl Promoter of Citrobacter freundii is Activated by the TyrR Protein," *J. Bacteriol.*, 179: 5914-5921 (1997).
Kirchner et al., "Phenol Hydroxylase from Bacillus thermoglucosidasius A7, a Two-protein Component Monooxygenase with a Dual Role for FAD*", *J. Biol. Chem.*, 278: 47545-47553 (2003).
Tover et al., "Growth medium composition-determined regulatory mechanisms are superimposed on CatR-mediated transcription from the pheBA and catBCA promoters in Pseudomonas putida," *Microbiology*, 147: 2149-2156 (2001).
Antson et al., "Three-Dimensional Structure of Tyrosine Phenol-lyase," *Biochemistry*, 32: 4195-4206 (1993).
Maruo et al., "Koso Handbook" *Asakura Shoten*, pp. 180 (1995).
International Preliminary Report on Patentability in corresponding PCT/JP2011/076484 dated Jun. 12, 2013. (English Translation).
Extended European Search Report in European Application No. 11842421.7 dated Apr. 4, 2014.
Sakai et al., "Effect of Lignocellulose-Derived Inhibitors on Growth of and Ethanol Production by Growth-Arrested Corynebacterium glutamicum R," *Appl. Environ. Microbiol.*, pp. 2349-2353 (2007).

\* cited by examiner

*Primary Examiner* — Maryam Monshipouri
(74) *Attorney, Agent, or Firm* — Marshall, Gerstein & Borun LLP

(57) ABSTRACT

Provided is a phenol-producing transformant constructed by transferring a gene which encodes an enzyme having tyrosine phenol-lyase activity into a coryneform bacterium as a host. Also provided is a process for producing phenol, which comprises a step of allowing the transformant to react in a reaction mixture containing tyrosine, a salt thereof, or an ester thereof under reducing conditions, and a step of collecting phenol from the reaction mixture.

10 Claims, 1 Drawing Sheet

ID NO: 16,
CORYNEFORM BACTERIUM TRANSFORMANT AND PROCESS FOR PRODUCING PHENOL USING THE SAME

This application is a 371 of PCT/JP2011/076484, filed Nov. 17, 2011, which claims foreign priority to Japanese application 2010-258089, filed Nov. 18, 2010.

TECHNICAL FIELD

The present invention relates to a technique for producing phenol. In more detail, the present invention relates to a coryneform bacterium transformant constructed by specific gene recombination and thereby provided with a phenol-producing function, and relates to an efficient phenol-producing process using the transformant.

BACKGROUND ART

Against the backdrop of global warming and exhaustion of fossil resources, production of chemical products using renewable resources, along with production of biofuels, is recognized as an emerging industry, biorefinery, which is an important means for realizing a low-carbon society, and has attracted keen attention.

However, production of biophenol using renewable resources is less productive as compared to production of lactic acid or ethanol because the metabolic reaction from a raw material saccharide consists of a great many steps. In addition, for the reasons that produced phenol inhibits bacterial proliferation and that phenol is cytotoxic, industrial production of phenol has been considered to be impossible.

Important use of phenol is phenol resins. A phenol resin, which is produced by addition condensation of phenol and aldehyde, is one of the oldest plastics, and with its properties including excellent heat resistance and durability, is used for various purposes, such as an alternative automotive material to metal, a semiconductor seal material, and a circuit board even today. Due to extremely high reactivity of phenol and aldehyde as raw materials and to the complicated three-dimensional network structure of resulting phenol resin polymers, precise structural designing and development into nanomaterials thereof had been considered difficult and so had been application to high-value-added use. However, in recent years, the theory of physical-properties of polymers and the simulation thereof have rapidly developed, and therefore it has gradually become possible to create highly functional materials from phenol resins by refining the network structure. Under the circumstances, the phenol resin production in Japan is also increasing year by year.

The currently employed industrial production process of phenol (cumene process) is a typical energy-consumptive process in the chemical industry using petroleum-derived benzene and propylene as raw materials, and requiring great amounts of solvent and thermal energy. Therefore, in the light of global environment conservation and greenhouse gas reduction, there is an urgent need to develop an environment-conscious, energy saving process that allows production of phenol from renewable resources and can reduce carbon dioxide emissions and waste products, that is, to establish biophenol production technologies.

There have not been reported phenol-producing bacteria in nature so far.

Also, there have not been known recombinant bacteria-based phenol-producing technologies to achieve a practically sufficient phenol productivity.

Tyrosine phenol-lyase is an enzyme that catalyzes synthesis of tyrosine from phenol, pyruvic acid, and ammonia and the reverse reaction thereof (for example, PTL 1). PTL 2, for example, teaches synthesis of tyrosine from phenol, pyruvic acid, and ammonia with the use of tyrosine phenol-lyase derived from members of the family Enterobacteriaceae.

Also, it is known that efficient tyrosine phenol-lyase production can be achieved by transformation of *Escherichia coli* with tyrosine phenol-lyase genes derived from various living things (PTL 3 to 5).

CITATION LIST

Patent Literature

[PTL 1] JP 2006-320238 A
[PTL 2] JP 08-154675 A
[PTL 3] JP 2005-278453 A
[PTL 4] WO 90/04031
[PTL 5] JP 04-218380 A

SUMMARY OF INVENTION

Technical Problem

An object of the present invention is to provide a microorganism capable of efficiently producing phenol from tyrosine, and a process for efficiently producing phenol from tyrosine.

Solution to Problem

The present inventors have wholeheartedly carried out investigations in order to achieve the object described above and obtained the following findings.
(i) A transformant constructed by transferring a tyrosine phenol-lyase gene into a coryneform bacterium can efficiently produce phenol from tyrosine.
(ii) The transformant can further efficiently produce phenol in the case where the phenol 2-monooxygenase gene (poxF) on the chromosome of the coryneform bacterium as the host has a disruption or deletion.
(iii) The transformant has a particularly higher phenol productivity when proliferation is substantially inhibited in a reaction mixture under reducing conditions.

The present invention, which has been completed based on the above-mentioned findings, provides the following transformant and process for producing phenol.
[1] A phenol-producing transformant constructed by transferring a gene which encodes an enzyme having tyrosine phenol-lyase activity into a coryneform bacterium as a host.
[2] The transformant of the above [1], wherein the gene which encodes an enzyme having tyrosine phenol-lyase activity is a gene derived from *Pantoea agglomerans*, a gene derived from *Citrobacter braakii*, a gene derived from *Desulfitobacterium hafniense*, a gene derived from *Chloroflexus aurantiacus*, a gene derived from *Nostoc punctiforme*, or a gene derived from *Treponema denticola*.
[3] The transformant of the above [1], wherein the gene which encodes an enzyme having tyrosine phenol-lyase activity is the DNA of the following (a) or (b).
(a) a DNA consisting of the base sequence of SEQ ID NO: 16, a DNA consisting of the base sequence of SEQ ID NO: 23, a DNA consisting of the base sequence of SEQ ID NO: 24, a DNA consisting of the base sequence of SEQ ID NO: 25, a DNA consisting of the base sequence of SEQ ID NO: 26, or a DNA consisting of the base sequence of SEQ ID NO: 27

(b) a DNA which hybridizes to a DNA consisting of a complementary base sequence of any of the DNAs of (a) under stringent conditions and which encodes a polypeptide having tyrosine phenol-lyase activity

[4] The transformant of any one of the above [1] to [3], wherein the coryneform bacterium as the host is a coryneform bacterium in which a gene which encodes an enzyme having phenol 2-monooxygenase activity on the chromosome is disrupted or deleted.

[5] The transformant of any one of the above [1] to [4], wherein the coryneform bacterium as the host is *Corynebacterium glutamicum*.

[6] The transformant of any one of the above [1] to [3], wherein the coryneform bacterium as the host is *Corynebacterium glutamicum* R (FERM BP-18976), ATCC13032, or ATCC13869.

[7] The transformant of any one of the above [1] to [3], wherein the coryneform bacterium as the host is a strain of *Corynebacterium glutamicum* R (FERM BP-18976), ATCC13032, or ATCC13869 in which a gene which encodes an enzyme having phenol 2-monooxygenase activity on the chromosome is disrupted or deleted.

[8] A *Corynebacterium glutamicum* transformant PHE31 (Accession Number: NITE BP-999).

[9] A process for producing phenol, which comprises a step of allowing the transformant of any one of the above [1] to [8] to react in a reaction mixture containing tyrosine, a salt thereof, or an ester thereof under reducing conditions, and a step of collecting phenol from the reaction mixture.

[10] The process of the above [9], wherein the transformant does not substantially proliferate in the reaction step.

[11] The process of the above [9] or [10], wherein the oxidation-reduction potential of the reaction mixture under reducing conditions is −200 mV to −500 mV.

Advantageous Effects of Invention

With the use of the transformant of the present invention, phenol can be efficiently produced from tyrosine.

Generally, growth of microorganisms is inhibited by a solvent, such as a phenol, because of its cytotoxicity, and therefore phenol production with the use of microorganisms was difficult. According to the process of the present invention, however, phenol production with the use of microorganisms can be achieved with a practically sufficient efficiency.

DESCRIPTION OF EMBODIMENTS

Figure 1:
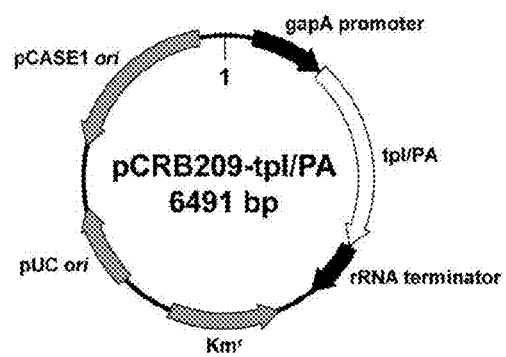
FIG. 1 shows the construct of a plasmid used in Examples.

Hereinafter, the present invention will be described in detail.
(I) Phenol-Producing Transformant
The transformant of the present invention capable of producing phenol is a transformant constructed by transferring a gene which encodes an enzyme having tyrosine phenol-lyase activity into a coryneform bacterium as a host.
Host
The coryneform bacterium is a group of microorganisms defined in Bergey's Manual of Determinative Bacteriology, Vol. 8, 599 (1974), and is not particularly limited as long as it proliferates under normal aerobic conditions.

The specific examples include *Corynebacterium, Brevibacterium, Arthrobacter, Mycobacterium* and *Micrococcus*. Among the coryneform bacteria, *Corynebacterium* is preferred.

Examples of the *Corynebacterium* include *Corynebacterium glutamicum, Corynebacterium efficiens, Corynebacterium ammoniagenes, Corynebacterium halotolerance*, and *Corynebacterium alkanolyticum*.

Inter alia, *Corynebacterium glutamicum* is preferred for safety and high phenol production. Examples of preferred strains include *Corynebacterium glutamicum* R (FERM P-18976), ATCC13032, ATCC13869, ATCC13058, ATCC13059, ATCC13060, ATCC13232, ATCC13286, ATCC13287, ATCC13655, ATCC13745, ATCC13746, ATCC13761, ATCC14020, ATCC31831, MJ-233 (FERM BP-1497), and MJ-233AB-41 (FERM BP-1498). Inter alia, strains R (FERM P-18976), ATCC13032, and ATCC13869 are preferred.

According to molecular biological classification, names of some species of coryneform bacteria, such as *Brevibacterium flavum, Brevibacterium lactofermentum, Brevibacterium divaricatum*, and *Corynebacterium lilium* are standardized to *Corynebacterium glutamicum* (Liebl, W. et al., Transfer of *Brevibacterium divaricatum* DSM 20297T, "*Brevibacterium flavum*" DSM 20411, "*Brevibacterium lactofermentum*" DSM 20412 and DSM 1412, and *Corynebacterium glutamicum* and their distinction by rRNA gene restriction patterns. Int. J. Syst. Bacteriol. 41: 255-260. (1991); and Kazuo Komagata et al., "Classification of the coryneform group of bacteria", Fermentation and industry, 45: 944-963 (1987)).

*Brevibacterium lactofermentum* ATCC13869, *Brevibacterium flavum* MJ-233 (FERM BP-1497) and MJ-233AB-41 (FERM BP-1498), etc. of the old classification are also suitable as *Corynebacterium glutamicum*.

Examples of the *Brevibacterium* include *Brevibacterium ammoniagenes* (for example, ATCC6872).

Examples of the *Arthrobacter* include *Arthrobacter globiformis* (for example, ATCC8010, ATCC4336, ATCC21056, ATCC31250, ATCC31738 and ATCC35698).

Examples of the *Mycobacterium* include *Mycobacterium bovis* (for example, ATCC19210 and ATCC27289).

Examples of the *Micrococcus* include *Micrococcus freudenreichii* (for example, NO. 239 (FERM P-13221)), *Micrococcus leuteus* (for example, NO. 240 (FERM P-13222)), *Micrococcus ureae* (for example, IAM1010), and *Micrococcus roseus* (for example, IFO3764).

The coryneform bacteria may be, let alone a wild strain, a mutant thereof or an artificial recombinant thereof. Examples thereof include disruptants in which a gene of lactate dehydrogenase, phosphoenolpyruvate carboxylase, or malate dehydrogenase is disrupted. Using such a disruptant as a host can improve phenol productivity and reduce production of by-products.

Inter alia, preferred is a disruptant in which a lactate dehydrogenase gene is disrupted. In the disruptant, the lactate dehydrogenase gene is disrupted and the metabolic pathway from pyruvic acid to lactic acid is blocked. Inter alia, especially preferred is a disruptant of *Corynebacterium glutamicum* R (FERM P-18976) strain in which the lactate dehydrogenase gene is disrupted.

Such a disruptant can be prepared based on a conventional gene engineering process. Such a lactate dehydrogenase disruptant and the preparation process thereof are described in WO 2005/010182 A1.

As shown in Example 3, the present inventors found that coryneform bacteria have significantly higher resistance to phenol as compared with other microorganisms. In this regard, coryneform bacteria are preferred in the production of phenol by the process of the present invention.

In addition, as compared with other aerobic microorganisms, coryneform bacteria can more efficiently produce substances under reducing conditions where the bacteria do not substantially proliferate. In this regard also, coryneform bacteria are preferred in the production of phenol by the process of the present invention.

Tyrosine Phenol-Lyase Gene (tpl)

Tyrosine phenol-lyase is an enzyme that catalyzes a reaction in which phenol is produced by elimination of pyruvic acid and ammonia from tyrosine and the reverse reaction thereof. Tyrosine phenol-lyase also catalyzes a reaction in which L-DOPA is produced from catechol and pyruvic acid.

The gene which encodes an enzyme having tyrosine phenol-lyase activity may be of any origin without particular limitation, and preferred are a gene derived from *Pantoea agglomerans*, a gene derived from *Citrobacter braakii*, a gene derived from *Desulfitobacterium hafniense*, a gene derived from *Chloroflexus aurantiacus*, a gene derived from *Nostoc punctiforme*, or a gene derived from *Treponema denticola*. Inter alia, more preferred is a gene derived from *Pantoea agglomerans*.

Examples of the gene derived from *Pantoea agglomerans* include the DNA consisting of the base sequence of SEQ ID NO: 16, examples of the gene derived from *Citrobacter braakii* include the DNA consisting of the base sequence of SEQ ID NO: 23, examples of the gene derived from *Desulfitobacterium hafniense* include the DNA consisting of the base sequence of SEQ ID NO: 24, examples of the gene derived from *Chloroflexus aurantiacus* include the DNA consisting of the base sequence of SEQ ID NO: 25, examples of the gene derived from *Nostoc punctiforme* include the DNA consisting of the base sequence of SEQ ID NO: 26, and examples of the gene derived from *Treponema denticola* include the DNA consisting of the base sequence of SEQ ID NO: 27.

In the present invention, a DNA which hybridizes to a DNA consisting of a complementary base sequence of the base sequence of SEQ ID NO: 16, 23, 24, 25, 26, or 27 under stringent conditions and which encodes a polypeptide having tyrosine phenol-lyase activity can also be used.

The "stringent conditions" as used herein means general conditions, for example, the conditions described in Molecular Cloning, A Laboratory Manual, Second edition, 1989, Vol. 2, p. 11. 45. It means, in particular, conditions where hybridization occurs at a temperature 5 to 10° C. below the melting temperature (Tm) of a perfect hybrid.

The tyrosine phenol-lyase activity can be measured by a modified method of the method described in J. Biol. Chem., 245, 1767-1772 (1970) "Materials and Methods". Briefly, by adding the test enzyme to a liquid for testing, a reaction mixture containing 50 mM potassium phosphate buffer at pH 8.0, 2.5 mM L-Tyr, 0.1 mM pyridoxal phosphate, 20% glycerol, and the enzyme was prepared, and the mixture was allowed to react at 30° C. for 30 minutes (0, 5, 10, 20, 30 minutes). The reaction was stopped by the addition of 0.6 N hydrochloric acid (final concentration). After the reaction mixture was subjected to centrifugation and filter filtration, the produced phenol was analyzed and quantified by HPLC (Cosmosil C18 ARII, mobile phase: 20% MeOH and 0.07% perchloric acid). The specific activity was calculated based on the initial rate of the reaction and the protein concentration (the amount of the enzyme required to produce 1 μmol of phenol per minute was defined as 1 unit).

In the present invention, a DNA consisting of a base sequence which has 90% or more, preferably 95% or more, more preferably 98% or more homology with the base sequence of SEQ ID NO: 16, 23, 24, 25, 26, or 27 and which encodes a polypeptide having tyrosine phenol-lyase activity can also be used.

In the present invention, the base sequence homology was calculated using GENETYX Ver. 8 (made by Genetyx).

The homolog of the DNA consisting of the base sequence of SEQ ID NO: 16, 23, 24, 25, 26, or 27 can be selected from a DNA library of a different species by, for example, PCR or hybridization using a primer or a probe designed based on these base sequences, according to a conventional method, and as a result, a DNA which encodes a polypeptide having tyrosine phenol-lyase activity can be obtained with a high probability.

Construction of Vector for Transformation

The DNA which encodes tyrosine phenol-lyase is amplified by PCR and then cloned into a suitable vector which is replicable in a host.

The plasmid vector may be any plasmid vector as long as it comprises a gene responsible for autonomously replicating function in a coryneform bacterium. Specific examples of the plasmid vector include pAM330 derived from *Brevibacterium lactofermentum* 2256 (JP 58-67699 A; Miwa, K. et al., Cryptic plasmids in glutamic acid-producing bacteria. Agric. Biol. Chem. 48:2901-2903 (1984); and Yamaguchi, R. et al., Determination of the complete nucleotide sequence of the *Brevibacterium lactofermentum* plasmid pAM330 and the analysis of its genetic information. Nucleic Acids Symp. Ser. 16:265-267 (1985)); pHM1519 derived from *Corynebacterium glutamicum* ATCC13058 (Miwa, K. et al., Cryptic plasmids in glutamic acid-producing bacteria. Agric. Biol. Chem. 48:2901-2903 (1984)) and pCRY30 derived from the same (Kurusu, Y. et al., Identification of plasmid partition function in coryneform bacteria. Appl. Environ. Microbiol. 57:759-764 (1991)); pCG4 derived from *Corynebacterium glutamicum* T250 (JP 57-183799 A; and Katsumata, R. et al., Protoplast transformation of glutamate-producing bacteria with plasmid DNA. J. Bacteriol., 159:306-311 (1984)), pAG1, pAG3, pAG14 and pAG50 derived from the same (JP 62-166890 A), and pEK0, pEC5 and pEKEx1 derived from the same (Eikmanns, B. J. et al., A family of *Corynebacterium glutamicum/Escherichia coli* shuttle vectors for cloning, controlled gene expression, and promoter probing. Gene, 102: 93-98 (1991)); etc.

Examples of a preferred promoter include promoter PgapA as a promoter of the glyceraldehyde-3-phosphate dehydrogenase A gene (gapA), promoter Pmdh as a promoter of the malate dehydrogenase gene (mdh), and promoter PldhA as a promoter of lactate dehydrogenase A gene (ldhA), all of which are derived from *Corynebacterium glutamicum* R, and inter alia, PgapA is preferred.

Examples of a preferred terminator include terminator rrnB T1T2 of *Escherichia coli* rRNA operon, terminator trpA of *Escherichia coli*, and terminator trp of *Brevibacterium lactofermentum*, and inter alia, terminator rrnB T1T2 is preferred.

Transformation

As a method of transformation, any publicly known method can be used without limitation. Examples of such a known method include the calcium chloride/rubidium chloride method, the calcium phosphate method, DEAE-dextran transfection, and electroporation. Inter alia, preferred for a coryneform bacterium is electroporation, which can be performed by a known method (Kurusu, Y. et al., Electroporation-transformation system for Coryneform bacteria by auxotrophic complementation., Agric. Biol. Chem. 54:443-447 (1990); and Vertes A. A. et al., Presence of mrr- and mcr-like restriction systems in Coryneform bacteria. Res. Microbiol. 144:181-185 (1993)).

The transformant is cultured using a culture medium usually used for culture of microorganisms. The culture medium may be a natural or synthetic medium containing a carbon source, a nitrogen source, inorganic salts, other nutritional substances, etc.

Examples of the carbon source include carbohydrates and sugar alcohols such as glucose, fructose, sucrose, mannose, maltose, mannitol, xylose, arabinose, galactose, starch, molasses, sorbitol and glycerol; organic acids such as acetic acid, citric acid, lactic acid, fumaric acid, maleic acid and gluconic acid; and alcohols such as ethanol and propanol. Hydrocarbons, such as normal paraffin, etc. may also be used as desired. These carbon sources may be used alone or as a mixture of two or more thereof. The concentration of these carbon sources in the culture medium is usually about 0.1 to 10 w/v %.

Examples of the nitrogen source include inorganic or organic ammonium compounds, such as ammonium chloride, ammonium sulfate, ammonium nitrate, and ammonium acetate; urea; aqueous ammonia; sodium nitrate; and potassium nitrate. Nitrogen-containing organic compounds, such as corn steep liquor, meat extract, peptone, N—Z-amine, protein hydrolysate, amino acid, etc. may also be used. These nitrogen sources may be used alone or as a mixture of two or more thereof. The concentration of these nitrogen sources in the culture medium varies depending on the kind of the nitrogen compound, but is usually about 0.1 to 10 w/v %.

Examples of the inorganic salts include potassium dihydrogen phosphate, dipotassium hydrogen phosphate, magnesium sulfate, sodium chloride, iron(II) nitrate, manganese sulfate, zinc sulfate, cobalt sulfate, and calcium carbonate. These inorganic salts may be used alone or as a mixture of two or more thereof. The concentration of the inorganic salts in the culture medium varies depending on the kind of the inorganic salts, but is usually about 0.01 to 1 w/v %.

Examples of the nutritional substances include meat extract, peptone, polypeptone, yeast extract, dry yeast, corn steep liquor, skim milk powder, defatted soybean hydrochloric acid hydrolysate, and extract from animals, plants or microorganisms, and degradation products thereof. The concentration of the nutritional substances in the culture medium varies depending on the kind of the nutritional substances, but is usually about 0.1 to 10 w/v %. Further, vitamins may be added as needed. Examples of the vitamins include biotin, thiamine (vitamin B1), pyridoxine (vitamin B6), pantothenic acid, inositol, nicotinic acid, etc.

The pH of the culture medium is preferably about 5 to 8.

Examples of the preferable microbial culture medium include A medium (Inui, M. et al., Metabolic analysis of *Corynebacterium glutamicum* during lactate and succinate productions under oxygen deprivation conditions. J. Mol. Microbiol. Biotechnol. 7:182-196 (2004)), BT medium (Omumasaba, C. A. et al., *Corynebacterium glutamicum* glyceraldehyde-3-phosphate dehydrogenase isoforms with opposite, ATP-dependent regulation. J. Mol. Microbiol. Biotechnol. 8:91-103 (2004)), etc.

The culture temperature is about 15 to 45° C., and the culture period is about 1 to 7 days.

Disruption or Deletion in Host Chromosomal Gene

In the coryneform bacterium as a host, the gene which encodes an enzyme having phenol 2-monooxygenase activity (poxF) on the chromosome preferably has a disruption or deletion for further efficient phenol production.

Replacement of a gene on the chromosome with the corresponding gene having an disruption or deletion can be achieved by creating a gene with deletion mutation for not allowing production of a normally functioning enzyme protein, and transforming a bacterium with a DNA comprising the mutated gene for recombination in which the gene on the chromosome and the mutated gene are exchanged. An enzyme protein encoded by a gene having a disruption or deletion, even when produced, has a conformation different from that of the wild type, and has no or reduced function. The gene deletion or gene disruption by way of such gene replacement through homologous recombination has already been established, and examples thereof include a method using a plasmid containing a temperature sensitive replication origin or a plasmid capable of conjugal transfer, and a method using a suicide vector not having a replication origin that works in a host (U.S. Pat. No. 6,303,383 and JP 05-007491 A).

Specifically, by the method described in Example 1, a coryneform bacterium in which the phenol 2-monooxygenase gene (poxF) is disrupted or deleted can be obtained.

(II) Process for Producing Phenol

Phenol can be produced by a process comprising a step of allowing the above-described transformant of the present invention to react in a reaction mixture containing tyrosine, and a step of collecting phenol from the reaction mixture.

Proliferation of Microorganism

Before the reaction, the transformant is preferably cultured and proliferated under aerobic conditions at about 25 to 38° C. for about 12 to 48 hours.

Culture Medium

The culture medium used for aerobic culture of the transformant before the reaction may be a natural or synthetic medium containing a carbon source, a nitrogen source, inorganic salts, other nutritional substances, etc.

Examples of the carbon source that can be used include saccharides (monosaccharides such as glucose, fructose, mannose, xylose, arabinose, and galactose; disaccharides such as sucrose, maltose, lactose, cellobiose, xylobiose, and trehalose; polysaccharides such as starch; and molasses); sugar alcohols such as mannitol, sorbitol, xylitol, and glycerol; organic acids such as acetic acid, citric acid, lactic acid, fumaric acid, maleic acid and gluconic acid; alcohols such as ethanol and propanol; and hydrocarbons such as normal paraffin.

These carbon sources may be used alone or as a mixture of two or more thereof.

Examples of the nitrogen source that can be used include inorganic or organic ammonium compounds, such as ammonium chloride, ammonium sulfate, ammonium nitrate, and ammonium acetate; urea; aqueous ammonia; sodium nitrate; and potassium nitrate. Nitrogen-containing organic compounds, such as corn steep liquor, meat extract, peptone, N—Z-amine, protein hydrolysate, amino acid, etc. may also be used. These nitrogen sources may be used alone or as a mixture of two or more thereof. The concentration of these nitrogen sources in the culture medium varies depending on the kind of the nitrogen compound, but is usually about 0.1 to 10 w/v %.

Examples of the inorganic salts include potassium dihydrogen phosphate, dipotassium hydrogen phosphate, magnesium sulfate, sodium chloride, iron(II) nitrate, manganese sulfate, zinc sulfate, cobalt sulfate, and calcium carbonate. These inorganic salts may be used alone or as a mixture of two or more thereof. The concentration of the inorganic salts in the culture medium varies depending on the kind of the inorganic salts, but is usually about 0.01 to 1 w/v %.

Examples of the nutritional substances include meat extract, peptone, polypeptone, yeast extract, dry yeast, corn steep liquor, skim milk powder, defatted soybean hydrochloric acid hydrolysate, and extract from animals, plants or microorganisms, and degradation products thereof. The concentration of the nutritional substances in the culture medium varies depending on the kind of the nutritional substances, but is usually about 0.1 to 10 w/v %.

Further, vitamins may be added as needed. Examples of the vitamins include biotin, thiamine (vitamin B1), pyridoxine (vitamin B6), pantothenic acid, inositol, nicotinic acid, etc.

The pH of the culture medium is preferably about 6 to 8.

Specific examples of the preferable culture medium for coryneform bacteria include A medium (Inui, M. et al., Metabolic analysis of *Corynebacterium glutamicum* during lactate and succinate productions under oxygen deprivation conditions. J. Mol. Microbiol. Biotechnol. 7:182-196 (2004)), BT medium (Omumasaba, C. A. et al., *Corynebacterium glutamicum* glyceraldehyde-3-phosphate dehydrogenase isoforms with opposite, ATP-dependent regulation. J. Mol. Microbiol. Biotechnol. 8:91-103 (2004)), etc. Such a culture medium can be used after prepared so as to contain a saccharide at a concentration in the above-mentioned range.

Reaction Mixture

As the reaction mixture, water, a buffer solution, an inorganic salt medium, or the like, containing a phenol precursor (raw material for phenol) can be used.

As the precursor, tyrosine (L-tyrosine, D-tyrosine, or a mixture thereof), a salt thereof, or an ester thereof may be used. Inter alia, preferred is L-tyrosine, a salt thereof, or an ester thereof. Examples of the salt include a sodium salt, a potassium salt, and a hydrochloride. Examples of the ester include esters with alcohols having 1 to 4 carbon atoms. Since tyrosine is poorly soluble in water, preferably used is a tyrosine salt, and more preferred is a sodium salt. These precursors may be used alone or a mixture of two or more kinds.

The concentration of tyrosine, a salt thereof, or an ester thereof in the reaction mixture is preferably about 0.5 to 10 w/v %, more preferably about 1 to 7 w/v %, and still more preferably about 2 to 5 w/v %. When the concentration is in the above range, phenol can be efficiently produced.

Examples of the buffer solution include a phosphate buffer, a Tris buffer, a carbonate buffer, etc. The concentration of the buffer solution is preferably about 10 to 150 mM.

Examples of the inorganic salt medium include a medium containing one or more kinds of inorganic salts including potassium dihydrogen phosphate, dipotassium hydrogen phosphate, magnesium sulfate, sodium chloride, iron(II) nitrate, manganese sulfate, zinc sulfate, cobalt sulfate, and calcium carbonate. Inter alia, preferred is a medium containing magnesium sulfate. Specific example of the inorganic salt medium include BT medium (Omumasaba, C. A. et al., *Corynebacterium glutamicum* glyceraldehyde-3-phosphate dehydrogenase isoforms with opposite, ATP-dependent regulation. J. Mol. Microbiol. Biotechnol. 8:91-103 (2004)) etc. The concentration of the inorganic salts in the culture medium varies depending on the kind of the inorganic salts, but is usually about 0.01 to 1 w/v %.

The pH of the reaction mixture is preferably about 6 to 8. During the reaction, the pH of the reaction mixture is preferably kept nearly neutral, in particular at around 7 with the use of aqueous ammonia, aqueous sodium hydroxide, or the like, under the control of a pH controller (for example, Type: DT-1023 made by Able).

Reaction Conditions

The reaction temperature, that is, the temperature for keeping the transformant alive during the reaction is preferably about 20 to 50° C., and more preferably about 25 to 47° C. When the temperature is in the above range, phenol can be efficiently produced.

The reaction period is preferably about 1 to 7 days, and more preferably about 1 to 3 days.

The culture may be a batch process, a fed-batch process, or a continuous process. Inter alia, a batch process is preferred.

<Reducing Conditions>

The reaction may be performed under aerobic conditions or reducing conditions, but preferably is performed under reducing conditions. Under reducing conditions, coryneform bacteria do not substantially proliferate and can further efficiently produce phenol.

The "reducing conditions" is defined based on the oxidation-reduction potential of the reaction mixture. The oxidation-reduction potential of the reaction mixture is preferably about −200 mV to −500 mV, and more preferably about −250 mV to −500 mV.

The reducing conditions of the reaction mixture can be simply estimated with the use of resazurin indicator (in reducing conditions, decolorization from blue to colorless is observed). However, for precise measurement, a redox-potential meter (for example, ORP Electrodes made by BROADLEY JAMES) is used.

As a method of preparing a reaction mixture under reducing conditions, any publicly known method can be used without limitation. For example, as a liquid medium for preparation of the reaction mixture, an aqueous solution for a reaction mixture may be used instead of distilled water or the like. As reference for preparation of the aqueous solution for a reaction mixture, for example, the method for preparing a culture medium for strictly anaerobic microorganisms, such as sulfate-reducing microorganisms (Pfennig, N. et al.: The dissimilatory sulfate-reducing bacteria, In The Prokaryotes, A Handbook on Habitats, Isolation and Identification of Bacteria, Ed. by Starr, M. P. et al. Berlin, Springer Verlag, 926-940, 1981, or *Nogeikagaku Jikkensho*, Ed. by Kyoto Daigaku Nogakubu Nogeikagaku Kyoshitsu, Vol. 3, Sangyo Tosho, 1990, Issue 26) may be used, and such a method provides an aqueous solution under desired reducing conditions.

Specifically, by treating distilled water or the like with heat or under reduced pressure for removal of dissolved gases, an aqueous solution for a reaction mixture under reducing conditions can be obtained. In this case, for removal of dissolved gases, especially dissolved oxygen, distilled water or the like may be treated under reduced pressure of about 10 mmHg or less, preferably about 5 mmHg or less, more preferably about 3 mmHg or less, for about 1 to 60 minutes, preferably for about 5 to 40 minutes.

Alternatively, by adding a suitable reducing agent (for example, thioglycolic acid, ascorbic acid, cysteine hydrochloride, mercaptoacetic acid, thiol acetic acid, glutathione, sodium sulfide, etc.), an aqueous solution for a reaction mixture under reducing conditions can be prepared.

These methods may be suitably combined to prepare an effective aqueous solution for a reaction mixture under reducing conditions.

It is preferred to maintain the reducing conditions of the reaction mixture during the reaction. For maintenance of reducing conditions, it is preferred that oxygen from the outside of the reaction system is prevented to the utmost extent from entering the system. Specific examples of the method employed for this purpose include a method comprising encapsulating the reaction system with inert gas, such as nitrogen gas, carbon dioxide gas, etc. In some cases, for allowing the metabolic functions in the cells of the aerobic bacterium of the present invention to work effectively during the reaction, addition of a solution of various nutrients or a reagent solution for adjusting and maintaining the pH of the reaction system may be needed. In such a case, for more effective prevention of oxygen incorporation, it is effective to remove oxygen in the solutions to be added, in advance.

Collection of Phenol

Through the culture performed in the above manner, phenol is produced in the reaction mixture. Phenol can be collected by collecting the reaction mixture, and it is also feasible to isolate phenol from the reaction mixture by a known method. Examples of such a known method include distillation, the membrane permeation method, and the organic solvent extraction method.

EXAMPLES

Hereinafter, the present invention will be described in more detail by way of Examples, but the present invention is not limited thereto.

Example 1

Cloning and Expression of Phenol-Producing Gene (1) Extraction of Chromosomal DNA from Microorganisms To extract chromosomal DNA from *Corynebacterium glutamicum* R (FERM P-18976), the bacterium was inoculated, with the use of a platinum loop, into A medium (2 g of $(NH_2)_2CO$, 7 g of $(NH_4)_2SO_4$, 0.5 g of $KH_2PO_4$, 0.5 g of $K_2HPO_4$, 0.5 g of $MgSO_4.7H_2O$, 1 mL of 0.06% (w/v) $Fe_2SO_4.7H_2O+0.042\%$ (w/v) $MnSO_4.2H_2O$, 1 mL of 0.02% (w/v) biotin solution, 2 mL of 0.01% (w/v) thiamin solution, 2 g of yeast extract, and 7 g of vitamin assay casamino acid were dissolved in 1 L of distilled water), which was supplemented with 50% (w/v) glucose as a carbon source to a final concentration of 4%, and cultured with shaking at 33° C. until the logarithmic growth phase. After the bacterial cells were collected, chromosomal DNA was recovered from the collected cells with the use of a DNA extraction kit (trade name: GenomicPrep Cells and Tissue DNA Isolation Kit, made by Amersham) according to the instruction manual.

To extract chromosomal DNA from *Pantoea agglomerans* NBRC12686, the bacterium was inoculated into NBRC Medium No. 802 (10 g of polypeptone, 2 g of yeast extract, and 1 g of $MgSO_4.7H_2O$ were dissolved in 1 L of distilled water) with the use of a platinum loop, and cultured with shaking at 30° C. until the logarithmic growth phase. After the bacterial cells were collected, chromosomal DNA was recovered from the collected cells with the use of a DNA extraction kit (trade name: GenomicPrep Cells and Tissue DNA Isolation Kit, made by Amersham) according to the instruction manual.

(2) Construction of Cloning Vectors

Construction of Cloning Vector pCRB22

A DNA fragment comprising a DNA replication origin sequence of pCASE1, a plasmid derived from *Corynebacterium casei* JCM12072 (hereinafter abbreviated as pCASE1-ori) and a DNA fragment comprising a cloning vector pHSG298 (made by Takara Bio, Inc.) were amplified by the following PCR method.

In the PCR, the following sets of primers were synthesized based on SEQ ID NO: 1 (pCASE1-ori sequence) and SEQ ID NO: 2 (cloning vector pHSG298) for cloning of the pCASE1-ori sequence and the cloning vector pHSG298, and were used.

Primers for pCASE1-ori sequence amplification (SEQ ID NO: 3)
(a-1); 5'-AT AGATCT AGAACGTCCGTAGGAGC-3'

(SEQ ID NO: 4)
(b-1); 5'-AT AGATCT GACTTGGTTACGATGGAC-3'

Primers (a-1) and (b-1) each have a BglII restriction enzyme site added thereto.

Primers for cloning vector pHSG298 amplification (SEQ ID NO: 5)
(a-2): 5'-AT AGATCT AGGTTTCCCGACTGGAAAG-3'

(SEQ ID NO: 6)
(b-2): 5'-AT AGATCT CGTGCCAGCTGCATTAATGA-3'

Primers (a-2) and (b-2) each have a BglII restriction enzyme site added thereto.

As the template DNA, total DNA extracted from *Corynebacterium casei* JCM12072 obtained from Japan Collection of Microorganisms (JCM) and cloning vector pHSG298 (made by Takara Bio, Inc.) were used.

Actual PCR was performed with the use of a thermal cycler, GeneAmp PCR System 9700 (made by Applied Biosystems) and TaKaRa LA Taq (made by Takara Bio, Inc.) as a reaction reagent under the conditions described below.

Reaction Mixture:

| | |
|---|---|
| TaKaRa LA Taq ™ (5 units/μL) | 0.5 μL |
| 10× LA PCR ™ Buffer II ($Mg^{2+}$ free) | 5 μL |
| 25 mM $MgCl_2$ | 5 μL |
| dNTP Mixture (2.5 mM each) | 8 μL |
| Template DNA | 5 μL (DNA content: 1 μg or less) |
| The above 2 primers*[)] | 0.5 μL each (final conc.: 1 μM) |
| Sterile distilled water | 25.5 μL |

The above ingredients were mixed, and 50 μL of the reaction mixture was subjected to PCR.
*[)]For amplification of the pCASE1-ori sequence, a combination of primers (a-1) and (b-1), and for amplification of the cloning vector pHSG298, a combination of primers (a-2) and (b-2) were used.

PCR Cycle:
Denaturation step: 94° C., 60 seconds
Annealing step: 52° C., 60 seconds
Extension step: 72° C.
pCASE1-ori sequence: 150 seconds
Cloning vector pHSG298: 180 seconds A cycle consisting of the above 3 steps was repeated 30 times.

Using 10 μL of the above-produced reaction mixture, 0.8% agarose gel electrophoresis was performed. In the case of the pCASE1-ori sequence, an about 1.4-kb DNA fragment was detected. In the case of the cloning vector pHSG298, an about 2.7-kb DNA fragment was detected.

10 μL of the about 1.4-kb DNA fragment comprising the pCASE1-ori sequence derived from *Corynebacterium casei*, and 10 μL of the about 2.7-kb DNA fragment comprising the cloning vector pHSG298, both amplified by the above PCR, were each cut with the use of restriction enzyme BglII and processed at 70° C. for 10 minutes for deactivation of the restriction enzyme. Both were mixed, and 1 μL of T4 DNA ligase 10× buffer solution and 1 unit of T4 DNA ligase (made by Takara Bio, Inc.) were added thereto. Sterile distilled water was added thereto so that the total volume was 10 μL, and the mixture was allowed to react at 15° C. for 3 hours for ligation. This was named Ligation Liquid A.

With the use of the Ligation Liquid A, *Escherichia coli* JM109 was transformed by the calcium chloride method (Journal of Molecular Biology, 53, 159 (1970)) and was applied to LB agar medium (1% polypeptone, 0.5% yeast extract, 0.5% sodium chloride, and 1.5% agar) containing 50 µg/mL of kanamycin.

A growing strain on the culture medium was subjected to liquid culture in the usual manner. Plasmid DNA was extracted from the culture and cut with the use of restriction enzyme BglII to confirm the inserted fragment. As a result, in addition to an about 2.7-kb DNA fragment of the cloning vector pHSG298, an about 1.4-kb DNA fragment of the pCASE-ori sequence was confirmed.

The cloning vector comprising the pCASE1-ori sequence was named pCRB22.

Construction of Cloning Vector pCRB207

A DNA fragment comprising a promoter sequence of the gapA gene encoding the glyceraldehyde-3-phosphate dehydrogenase (hereinafter abbreviated as PgapA) derived from *Corynebacterium glutamicum* R, and a DNA fragment comprising an rrnBT1T2 bidirectional terminator sequence (hereinafter abbreviated as terminator sequence) derived from a cloning vector pKK223-3 (made by Pharmacia) were amplified by the following method.

In the PCR, the following sets of primers were synthesized based on SEQ ID NO: 7 (PgapA sequence) and SEQ ID NO: 8 (terminator sequence) for cloning of the PgapA sequence and the terminator sequence, and were used.

Primers for PgapA Sequence Amplification

```
                                              (SEQ ID NO: 9)
(a-3); 5'-CTCT GTCGAC CCGAAGATCTGAAGATTCCTG-3'

(SEQ ID NO: 10)
(b-3); 5'-CTCT GTCGAC GGATCC CCATGG
TGTGTCTCCTCTAAAGATTGTAGG-3'
```

Primer (a-3) has a SalI restriction enzyme site added thereto, and primer (b-3) has SalI, BamHI, and NcoI restriction enzyme sites added thereto.

Primers for Terminator Sequence Amplification

```
                                              (SEQ ID NO: 11)
(a-4); 5'-CTCT GCATGC
CCATGG CTGTTTTGGCGGATGAGAGA-3'

(SEQ ID NO: 12)
(b-4); 5'-CTCT GCATGC TCATGA
AAGAGTTTGTAGAAACGCAAAAAGG-3'
```

Primer (a-4) has SphI and NcoI restriction enzyme sites added thereto, and primer (b-4) has SphI and BspHI restriction enzyme sites added thereto.

As the template DNA, the chromosomal DNA extracted from *Corynebacterium glutamicum* R (FERM P-18976) and the plasmid pKK223-3 (made by Pharmacia) were used.

Actual PCR was performed with the use of a thermal cycler, GeneAmp PCR System 9700 (made by Applied Biosystems) and TaKaRa LA Taq (made by Takara Bio, Inc.) as a reaction reagent under the conditions described below.

Reaction Mixture:

| | |
|---|---|
| TaKaRa LA Taq ™ (5 units/µL) | 0.5 µL |
| 10× LA PCR ™ Buffer II (Mg²⁺ free) | 5 µL |

-continued

| | |
|---|---|
| 25 mM MgCl$_2$ | 5 µL |
| dNTP Mixture (2.5 mM each) | 8 µL |
| Template DNA | 5 µL (DNA content: 1 µg or less) |
| The above 2 primers*⁾ | 0.5 µL each (final conc.: 1 µM) |
| Sterile distilled water | 25.5 µL |

The above ingredients were mixed, and 50 µL of the reaction mixture was subjected to PCR.
*⁾For amplification of the PgapA sequence, a combination of primers (a-3) and (b-3), and for amplification of the terminator sequence, a combination of primers (a-4) and (b-4) were used.

PCR Cycle:
Denaturation step: 94° C., 60 seconds
Annealing step: 52° C., 60 seconds
Extension step: 72° C.
PgapA sequence: 45 seconds
Terminator sequence: 30 seconds
A cycle consisting of the above 3 steps was repeated 30 times.

Using 10 µL of the above-produced reaction mixture, 0.8% agarose gel electrophoresis was performed. In the case of the PgapA sequence, an about 0.6-kb DNA fragment was detected. In the case of the terminator sequence, an about 0.4-kb DNA fragment was detected.

10 µL of the about 0.6-kb DNA fragment comprising the PgapA sequence derived from *Corynebacterium glutamicum* R, which was amplified by the above PCR, and the about 4.1-kb cloning vector pCRB22 were each cut with the use of restriction enzyme SalI and processed at 70° C. for 10 minutes for deactivation of the restriction enzyme. Both were mixed, and 1 µL of T4 DNA ligase 10× buffer solution and 1 unit of T4 DNA ligase (made by Takara Bio, Inc.) were added thereto. Sterile distilled water was added thereto so that the total volume was 10 µL, and the mixture was allowed to react at 15° C. for 3 hours for ligation. This was named Ligation Liquid B.

With the use of the Ligation Liquid B, *Escherichia coli* JM109 was transformed by the calcium chloride method (Journal of Molecular Biology, 53, 159 (1970)) and was applied to LB agar medium (1% polypeptone, 0.5% yeast extract, 0.5% sodium chloride, and 1.5% agar) containing 50 µg/mL of kanamycin.

A growing strain on the culture medium was subjected to liquid culture in the usual manner. Plasmid DNA was extracted from the culture and cut with the use of restriction enzyme SalI to confirm the inserted fragment. As a result, in addition to an about 4.1-kb DNA fragment of the cloning vector pCRB22, an about 0.6-kb DNA fragment of the PgapA sequence was confirmed.

The cloning vector comprising the PgapA sequence was named pCRB206.

10 µL of the about 0.4-kb DNA fragment comprising the terminator sequence derived from the plasmid pKK223-3, which was amplified by the above PCR, was cut with the use of restriction enzymes NcoI and BspHI, 2 µL of the above cloning vector pCRB206 was cut with the use of restriction enzyme NcoI, and both were processed at 70° C. for 10 minutes for deactivation of the restriction enzymes. Both were mixed, and 1 µL of T4 DNA ligase 10× buffer solution and 1 unit of T4 DNA ligase (made by Takara Bio, Inc.) were added thereto. Sterile distilled water was added thereto so that the total volume was 10 µL, and the mixture was allowed to react at 15° C. for 3 hours for ligation. This was named Ligation Liquid C.

With the use of the Ligation Liquid C, *Escherichia coli* JM109 was transformed by the calcium chloride method (Journal of Molecular Biology, 53, 159 (1970)) and was applied to LB agar medium (1% polypeptone, 0.5% yeast extract, 0.5% sodium chloride, and 1.5% agar) containing 50 μg/mL of kanamycin.

A growing strain on the culture medium was subjected to liquid culture in the usual manner. Plasmid DNA was extracted from the culture and cut with the use of the restriction enzyme to confirm the inserted fragment. As a result, in addition to an about 4.7-kb DNA fragment of the cloning vector pCRB206, an about 0.4-kb DNA fragment of the terminator sequence was confirmed.

The cloning vector comprising the rrnBT1T2 terminator sequence was named pCRB207.

Construction of Cloning Vector pCRB209

A DNA fragment comprising a promoter sequence of the gapA (glyceraldehyde 3-phosphate dehydrogenase A) gene (hereinafter abbreviated as PgapA) derived from *Corynebacterium glutamicum* R was amplified by the following method.

In the PCR, the following set of primers was synthesized based on SEQ ID NO: 13 (pCRB207) for cloning of the pCRB207 sequence, and was used.

Primers for pCRB207 Sequence Amplification

```
                                         (SEQ ID NO: 14)
(a-5); 5'-CTCT CATATG CTGTTTTGGCGGATGAGAG-3'

(SEQ ID NO: 15)
(b-5); 5'-CTCT CATATG GTGTCTCCTCTAAAGATTGTAGG-3'
```

Primers (a-5) and (b-5) each have an NdeI restriction enzyme site added thereto.

As the template DNA, the cloning vector pCRB207 comprising a gapA promoter and a rrnBT1T2 terminator sequence was used.

Actual PCR was performed with the use of a thermal cycler, GeneAmp PCR System 9700 (made by Applied Biosystems) and TaKaRa LA Taq (made by Takara SHUZO) as a reaction reagent under the conditions described below.

Reaction Mixture:

| | |
|---|---|
| TaKaRa LA Taq ™ (5 units/μL) | 0.5 μL |
| 10× LA PCR ™ Buffer II (Mg²⁺ free) | 5 μL |
| 25 mM MgCl₂ | 5 μL |
| dNTP Mixture (2.5 mM each) | 8 μL |
| Template DNA | 5 μL (DNA content: 1 μg or less) |
| The above 2 primers*⁾ | 0.5 μL each (final conc.: 1 μM) |
| Sterile distilled water | 25.5 μL |

The above ingredients were mixed, and 50 μL of the reaction mixture was subjected to PCR.
*⁾For amplification of the pCRB207 sequence, a combination of primers (a-5) and (b-5) was used.

PCR Cycle:
Denaturation step: 94° C., 60 seconds
Annealing step: 52° C., 60 seconds
Extension step: 72° C., 307 seconds
A cycle consisting of the above 3 steps was repeated 30 times.

Using 10 μL of the above-produced reaction mixture, 0.8% agarose gel electrophoresis was performed, and an about 5.1-kb DNA fragment comprising the cloning vector pCRB207 was detected.

10 μL of the about 5.1-kb DNA fragment comprising the gene derived from pCRB207, which was amplified by the above PCR, was cut with the use of restriction enzyme NdeI and processed at 70° C. for 10 minutes for deactivation of the restriction enzyme. To this, 1 μL of T4 DNA ligase 10× buffer solution and 1 unit of T4 DNA ligase (made by Takara SHUZO) were added. Sterile distilled water was added thereto so that the total volume was 10 μL, and the mixture was allowed to react at 15° C. for 3 hours for ligation. This was named Ligation Liquid D.

With the use of the Ligation Liquid D, *Escherichia coli* JM109 was transformed by the calcium chloride method (Journal of Molecular Biology, 53, 159 (1970)) and was applied to LB agar medium (1% polypeptone, 0.5% yeast extract, 0.5% sodium chloride, and 1.5% agar) containing 50 μg/mL of kanamycin.

A growing strain on the culture medium was subjected to liquid culture in the usual manner. Plasmid DNA was extracted from the culture and cut with the use of restriction enzyme NdeI to confirm the inserted restriction enzyme site.

The cloning vector comprising the PgapA sequence and the rrnBT1T2 terminator sequence was named pCRB209.

(3) Cloning of Phenol-Producing Gene

Cloning of Phenol-Producing Gene Derived from *Pantoea agglomerans*

A DNA fragment comprising the tpl gene which is derived from *Pantoea agglomerans* and which encodes a gene having tyrosine phenol-lyase activity was amplified by the PCR method as described below.

In the PCR, the following set of primers was synthesized based on SEQ ID NO: 16 (the tpl gene of *Pantoea agglomerans*) with the use of "394 DNA/RNA Synthesizer" made by Applied Biosystems for cloning of the tpl gene, and was used.

Primers for tpl Gene Amplification

```
                                         (SEQ ID NO: 17)
(a-6); 5'-CTCT CATATG AACTATCCTGCCGAGC-3'

(SEQ ID NO: 18)
(b-6); 5'-CTCT CATATG

TTAAATAAAGTCAAAACGCGCAGTAAAG-3'
```

Primers (a-6) and (b-6) each have an NdeI restriction enzyme site added thereto.

As the template DNA for *Pantoea agglomerans*, the chromosomal DNA extracted from *Pantoea agglomerans* NBRC12686 obtained from NITE Biological Resource Center (NBRC) was used.

Actual PCR was performed with the use of a thermal cycler, GeneAmp PCR System 9700 (made by Applied Biosystems) and TaKaRa LA Taq (made by Takara Bio, Inc.) as a reaction reagent under the conditions described below.

Reaction Mixture:

| | |
|---|---|
| TaKaRa LA Taq ™ (5 units/μL) | 0.5 μL |
| 10× LA PCR ™ Buffer II (Mg²⁺ free) | 5 μL |
| 25 mM MgCl₂ | 5 μL |
| dNTP Mixture (2.5 mM each) | 8 μL |
| Template DNA | 5 μL (DNA content: 1 μg or less) |
| The above 2 primers*⁾ | 0.5 μL each (final conc.: 1 μM) |
| Sterile distilled water | 25.5 μL |

The above ingredients were mixed, and 50 μL of the reaction mixture was subjected to PCR.
*⁾For amplification of the tpl gene of *Pantoea agglomerans*, a combination of primers (a-6) and (b-6) was used.

PCR Cycle:
Denaturation step: 94° C., 60 seconds
Annealing step: 52° C., 60 seconds
Extension step: 72° C.
*Pantoea agglomerans* tpl gene 82 seconds
A cycle consisting of the above 3 steps was repeated 30 times.

With the use of 10 μl of the reaction mixture produced above, 0.8% agarose gel electrophoresis was performed. As a result, detected was an about 1.4-kb DNA fragment of the *Pantoea agglomerans* tpl gene.

(4) Construction of Phenol-Producing Gene Expression Plasmid

Cloning of Phenol-Producing Gene to pCRB209

10 µL of the about 1.4-kb DNA fragment comprising the tpl gene derived from *Pantoea agglomerans* amplified by the PCR in the above (3), and 2 µL of the cloning vector pCRB209 comprising promoter PgapA were each cut with the use of restriction enzyme NdeI, and were processed at 70° C. for 10 minutes for deactivation of the restriction enzyme. Both were mixed, and 1 µL of T4 DNA ligase 10× buffer solution and 1 unit of T4 DNA ligase (made by Takara Bio, Inc.) were added thereto. Sterile distilled water was added thereto so that the total volume was 10 µL, and the mixture was allowed to react at 15° C. for 3 hours for ligation. The resulting liquid was named Ligation Liquid E.

With the use of the obtained Ligation Liquid E, *Escherichia coli* JM109 was transformed by the calcium chloride method (Journal of Molecular Biology, 53, 159 (1970)) and was applied to LB agar medium (1% polypeptone, 0.5% yeast extract, 0.5% sodium chloride, and 1.5% agar) containing 50 µg/mL of kanamycin.

A growing strain on the culture medium was subjected to liquid culture in the usual manner. Plasmid DNA was extracted from the culture and cut with the use of restriction enzyme to confirm the inserted fragment. As a result, in addition to an about 5.1-kb DNA fragment of the plasmid pCRB209, confirmed was an about 1.4-kb inserted fragment of the tpl gene derived from *Pantoea agglomerans* (Ligation Liquid E).

The plasmid comprising the tpl gene derived from *Pantoea agglomerans* was named pCRB209-tpl/PA (FIG. 1).

(5) Construction of Plasmid for *Corynebacterium glutamicum* Chromosomal Gene Disruption Construction of Plasmid for *Corynebacterium glutamicum* poxF Gene Disruption A DNA fragment required for constructing a plasmid for markerless disruption of the poxF gene on the chromosome of *Corynebacterium glutamicum* was amplified by the PCR method as described below.

In the PCR, the following sets of primers were synthesized based on the sequence of *Corynebacterium glutamicum* R with the use of "394 DNA/RNA Synthesizer" made by Applied Biosystems, and were used.

Primers for Amplification of poxF-1 Region

```
                                        (SEQ ID NO: 19)
(a-7); 5'-CTCT TCTAGA TACGTCCTAAACACCCGAC-3'

(b-7);
                                        (SEQ ID NO: 20)
5'-GACCAACCATTGCTGACTTGCGTATCCATAGTCAGGCTTC-3'
```

Primer (a-7) has an XbaI restriction enzyme site added thereto.

Primers for Amplification of poxF-2 Region

```
                                        (SEQ ID NO: 21)
(a-8); 5'-CAAGTCAGCAATGGTTGGTC-3'

(SEQ ID NO: 22)
(b-8); 5'-CTCT TCTAGA TGATCAGTACCAAGGGTGAG-3'
```

Primer (b-8) has an XbaI restriction enzyme site added thereto.

As the template DNA, the chromosomal DNA extracted from *Corynebacterium glutamicum* R was used.

Actual PCR was performed with the use of a thermal cycler, GeneAmp PCR System 9700 (made by Applied Biosystems) and TaKaRa LA Taq (made by Takara Bio, Inc.) as a reaction reagent under the conditions described below.

Reaction Mixture:

| | |
|---|---|
| TaKaRa LA Taq ™ (5 units/µL) | 0.5 µL |
| 10× LA PCR ™ Buffer II (Mg²⁺ free) | 5 µL |
| 25 mM MgCl₂ | 5 µL |
| dNTP Mixture (2.5 mM each) | 8 µL |
| Template DNA | 5 µL (DNA content: 1 µg or less) |
| The above 2 primers*⁾ | 0.5 µL each (final conc.: 1 µM) |
| Sterile distilled water | 25.5 µL |

The above ingredients were mixed, and 50 µL of the reaction mixture was subjected to PCR.
*⁾For amplification of the poxF-1 region, a combination of primers (a-7) and (b-7), and for amplification of the poxF-2 region, a combination of primers (a-8) and (b-8) were used.

PCR Cycle:
Denaturation step: 94° C., 60 seconds
Annealing step: 52° C., 60 seconds
Extension step: 72° C.
poxF-1 region: 50 seconds
poxF-2 region: 50 seconds
A cycle consisting of the above 3 steps was repeated 30 times.

Using 10 µL of the above-produced reaction mixture, 0.8% agarose gel electrophoresis was performed. An about 0.8-kb DNA fragment in the case of the *Corynebacterium glutamicum* poxF-1 region, and an about 0.8-kb DNA fragment in the case of the poxF-2 region were detected.

Subsequently, 1 µL each of the poxF-1 region fragment and the poxF-2 region fragment, which were amplified by the above PCR, were mixed and subjected to PCR for ligation.

Actual PCR was performed with the use of a thermal cycler, GeneAmp PCR System 9700 (made by Applied Biosystems) and TaKaRa LA Taq (made by Takara Bio, Inc.) as a reaction reagent under the conditions described below.

Reaction Mixture:

| | |
|---|---|
| TaKaRa LA Taq ™ (5 units/µL) | 0.5 µL |
| 10× LA PCR ™ Buffer II (Mg²⁺ free) | 5 µL |
| 25 mM MgCl₂ | 5 µL |
| dNTP Mixture (2.5 mM each) | 8 µL |
| The above 2 fragments*⁾ | 1 µL each |
| Sterile distilled water | 29.5 µL |

The above ingredients were mixed, and 50 µL of the reaction mixture was subjected to PCR.
*⁾poxF-1 region fragment and poxF-2 region fragment were used.

PCR Cycle:
Denaturation step: 95° C., 20 seconds
Annealing step: 52° C., 5 seconds
Extension step: 72° C., 50 seconds
A cycle consisting of the above 3 steps was repeated 30 times.

Further, using, as the template DNA, the obtained fragment in which poxF-1 and poxF-2 were ligated, a poxF deletion fragment was amplified by PCR.

Actual PCR was performed with the use of a thermal cycler, GeneAmp PCR System 9700 (made by Applied Biosystems) and TaKaRa LA Taq (made by Takara Bio, Inc.) as a reaction reagent under the conditions described below.

Reaction Mixture:

| | |
|---|---|
| TaKaRa LA Taq ™ (5 units/µL) | 0.5 µL |
| 10× LA PCR ™ Buffer II (Mg²⁺ free) | 5 µL |

| | |
|---|---|
| 25 mM MgCl$_2$ | 5 μL |
| dNTP Mixture (2.5 mM each) | 8 μL |
| Template DNA | 5 μL (DNA content: 1 μg or less) |
| The above 2 primers*[)] | 0.5 μL each (final conc.: 1 μM) |
| Sterile distilled water | 25.5 μL |

The above ingredients were mixed, and 50 μL of the reaction mixture was subjected to PCR.
*[)]For amplification of the poxF deletion fragment, a combination of primers (a-7) and (b-8) was used.

PCR Cycle:
Denaturation step: 95° C., 20 seconds
Annealing step: 52° C., 5 seconds
Extension step: 72° C., 50 seconds A cycle consisting of the above 3 steps was repeated 30 times.

Using 10 μL of the above-produced reaction mixture, 0.8% agarose gel electrophoresis was performed, and an about 1.6-kb fragment of the poxF deletion fragment was detected.

10 μL of the about 1.7-kb DNA fragment of the poxF deletion fragment derived from *Corynebacterium glutamicum* R, which was amplified by the above PCR, and 2 μL of an about 4.4-kb plasmid pCRA725 for markerless chromosomal gene transfection (J. Mol. Microbial. Biotechnol., Vol. 8, 243-254, 2004 (JP 2006-124440A) were each cut with the use of restriction enzyme XbaI, and processed at 70° C. for 10 minutes for deactivation of the restriction enzyme. Both were mixed, and 1 μL of T4 DNA ligase 10× buffer solution and 1 unit of T4 DNA ligase (made by Takara Bio, Inc.) were added thereto. Sterile distilled water was added thereto so that the total volume was 10 μL, and the mixture was allowed to react at 15° C. for 3 hours for ligation. This was named Ligation Liquid F.

With the use of the Ligation Liquid F, *Escherichia coli* JM109 was transformed by the calcium chloride method (Journal of Molecular Biology, 53, 159 (1970)) and was applied to LB agar medium (1% polypeptone, 0.5% yeast extract, 0.5% sodium chloride, and 1.5% agar) containing 50 μg/mL of kanamycin.

A growing strain on the culture medium was subjected to liquid culture in the usual manner. Plasmid DNA was extracted from the culture and cut with the use of restriction enzyme XbaI to confirm the inserted fragment. As a result, in addition to an about 4.4-kb DNA fragment of the plasmid pCRA725, an about 1.7-kb inserted fragment of the poxF deletion gene derived from *Corynebacterium glutamicum* (Ligation Liquid F) was confirmed.

The plasmid comprising the poxF deletion gene derived from *Corynebacterium glutamicum* was named pCRA725-poxF/CG.

(6) Construction of Strain in which a Gene Associated with Degradation of Phenol is Disrupted Vector pCRA725 for markerless chromosomal gene transfection is a plasmid that cannot be replicated within *Corynebacterium glutamicum* R. With the use of the plasmid pCRA725-poxF/CG, transformation of *Corynebacterium glutamicum* R was performed by electroporation (Agric. Biol. Chem., Vol. 54, 443-447 (1990) and Res. Microbiol., Vol. 144, 181-185 (1993)), and the strain was applied to A agar medium (A liquid medium and 1.5% agar) containing 50 μg/mL of kanamycin. The single crossover strain obtained on the above medium was applied to BT agar medium (2 g of (NH$_2$)$_2$CO, 7 g of (NH$_4$)$_2$SO$_4$, 0.5 g of KH$_2$PO$_4$, 0.5 g of K$_2$HPO$_4$, 0.5 g of MgSO$_4$.7H$_2$O, 1 mL of 0.06% (w/v) Fe$_2$SO$_4$.7H$_2$O+0.042% (w/v) MnSO$_4$.2H$_2$O, 1 mL of 0.02% (w/v) biotin solution, 2 mL of 0.01% (w/v) thiamin solution dissolved in 1 L of distilled water, and 1.5% agar) containing 10% (w/v) sucrose.

In the case of a strain having a single crossover of the plasmid pCRA725-poxF/CG with the homologous region on the chromosome, the strain shows kanamycin resistance resulting from the expression of the kanamycin resistance gene on the pCRA725-poxF/CG and mortality on a culture medium containing sucrose resulting from the expression of the *Bacillus subtilis* sacR-sacB gene. In the case of a strain having a double crossover of the plasmid pCRA725-poxF/CG, the strain shows kanamycin sensitivity resulting from the loss of the kanamycin resistance gene on the pCRA725-poxF/CG and growing ability on a culture medium containing sucrose resulting from the loss of the sacR-sacB gene. The markerless chromosomal gene disruptant shows kanamycin sensitivity and growing ability on a culture medium containing sucrose. Therefore, a strain that showed kanamycin sensitivity and growing ability on a culture medium containing sucrose was selected.

The obtained markerless poxF gene disruptant of *Corynebacterium glutamicum* R was named *Corynebacterium glutamicum* ΔpoxF.

(7) Construction of Transgenic Strain for Phenol-Producing Gene

With the use of the above-described plasmid pCRB209-tpl/PA, transformation of *Corynebacterium glutamicum* ΔpoxF was performed by electroporation (Agric. Biol. Chem., Vol. 54, 443-447 (1990) and Res. Microbiol., Vol. 144, 181-185 (1993)), and the strain was applied to A agar medium containing 50 μg/mL of kanamycin.

A growing strain on the culture medium was subjected to liquid culture in the usual manner. Plasmid DNA was extracted from the culture and cut with the use of restriction enzyme to confirm the inserted plasmid. As a result, transfection of the above-constructed plasmid pCRB209-tpl/PA was confirmed.

The obtained strain was named *Corynebacterium glutamicum* PHE31.

*Corynebacterium glutamicum* PHE31 was deposited in Incorporated Administrative Agency National Institute of Technology and Evaluation, NITE Patent Microorganisms Depositary (2-5-8 Kazusakamatari, Kisarazu-shi, Chiba 292-0818 Japan) under Accession Number NITE BP-999 on Nov. 2, 2010.

Example 2

Experiment of Phenol Production Using *Corynebacterium glutamicum* Phenol-Producing Gene Transgenic Strain and *Corynebacterium glutamicum* by-Product Formation Pathway Disruptant The *Corynebacterium glutamicum* PHE31 (the markerless chromosomal poxF gene disruptant transfected with phenol-producing gene expression plasmid pCRB209-tpl/PA) prepared in Example 1 was applied to A agar medium (2 g of (NH$_2$)$_2$CO, 7 g of (NH$_4$)$_2$SO$_4$, 0.5 g of KH$_2$PO$_4$, 0.5 g of K$_2$HPO$_4$, 0.5 g of MgSO$_4$.7H$_2$O, 1 mL of 0.06% (w/v) Fe$_2$SO$_4$.7H$_2$O+0.042% (w/v) MnSO$_4$.2H$_2$O, 1 mL of 0.02% (w/v) biotin solution, 2 mL of 0.01% (w/v) thiamin solution, 2 g of yeast extract, 7 g of vitamin assay casamino acid, 40 g of glucose, and 15 g of agar were suspended in 1 L of distilled water) containing 50 μg/mL of kanamycin, and left stand in the dark at 28° C. for 20 hours.

An inoculation loop of the *Corynebacterium glutamicum* PHE31 grown on a plate as above was inoculated into a test tube containing 10 mL of A liquid medium containing 50 μg/mL of kanamycin, and aerobically cultured with shaking at 28° C. for 15 hours.

The *Corynebacterium glutamicum* PHE31 grown in the above conditions was inoculated into a 2 L-conical flask containing 500 mL of A liquid medium containing 50 μg/mL of kanamycin, and aerobically cultured with shaking at 28° C. for 15 hours.

The bacterial cells cultured and proliferated as above were collected by centrifugation (5,000×g at 4° C. for 15 minutes). The obtained bacterial cells were suspended in 50 mL of BT (-urea) liquid medium (0.7% ammonium sulfate, 0.05% potassium dihydrogen phosphate, 0.05% dipotassium hydrogen phosphate, 0.05% magnesium sulfate heptahydrate, 0.0006% iron sulfate heptahydrate, 0.00042% manganese sulfate hydrate, 0.00002% biotin and 0.00002% thiamine hydrochloride) so that the final concentration of the bacterial cell was 10%. To a 100-mL medium bottle, the cell suspension was transferred, L-tyrosine disodium salt was added as a substrate, and the reaction was allowed to proceed under reducing conditions (the ORP of the reaction mixture: −450 mV) in a water bath kept at 33° C. with stirring. As for the addition of L-tyrosine disodium salt, 40 mM L-tyrosine disodium salt was added at 0, 1, 3, and 10 hours after the start of the reaction.

A sample of the reaction mixture was centrifuged (15,000×g at 4° C. for 10 minutes), and the obtained supernatant was used for quantitative determination of phenol.

As a result, in the reaction under reducing conditions, *Corynebacterium glutamicum* PHE31 had produced 34 mM of phenol in 24 hours.

Example 3

Test for Suitability as a Host for Phenol Production Influence of Phenol on Aerobic Proliferation A growth inhibition test in aerobic culture was performed to examine the influence of phenol on *Corynebacterium glutamicum*, *Escherichia coli*, and *Pseudomonas putida*. *Pseudomonas putida* S12, which was used for the test, is reported to be a solvent-resistant strain. In the report, disclosed is an unparalleled technology using the strain as a host in phenol production.

*Corynebacterium glutamicum* R was applied to A agar medium (2 g of $(NH_2)_2CO$, 7 g of $(NH_4)_2SO_4$, 0.5 g of $KH_2PO_4$, 0.5 g of $K_2HPO_4$, 0.5 g of $MgSO_4.7H_2O$, 1 mL of 0.06% (w/v) $Fe_2SO_4.7H_2O$+0.042% (w/v) $MnSO_4.2H_2O$, 1 mL of 0.02% (w/v) biotin solution, 2 mL of 0.01% (w/v) thiamin solution, 2 g of yeast extract, 7 g of vitamin assay casamino acid, 40 g of glucose, and 15 g of agar were suspended in 1 L of distilled water) and was left stand in the dark at 33° C. for 15 hours.

An inoculation loop of the *Corynebacterium glutamicum* R grown on a plate as above was inoculated into a test tube containing 10 mL of A liquid medium (2 g of $(NH_2)_2CO$, 7 g of $(NH_4)_2SO_4$, 0.5 g of $KH_2PO_4$, 0.5 g of $K_2HPO_4$, 0.5 g of $MgSO_4.7H_2O$, 1 mL of 0.06% (w/v) $Fe_2SO_4.7H_2O$+0.042% (w/v) $MnSO_4.2H_2O$, 1 mL of 0.02% (w/v) biotin solution, 2 mL of 0.01% (w/v) thiamin solution, 2 g of yeast extract, 7 g of vitamin assay casamino acid, and 40 g of glucose were suspended in 1 L of distilled water) and was aerobically cultured with shaking at 33° C. for 13 hours.

The *Corynebacterium glutamicum* R grown in the above conditions was inoculated into 100 mL of A liquid medium in such a way that the initial bacterial cell concentration would be $OD_{610}$=0.05, phenol was added at the same time in such a way that the final concentration would be 0, 0.16, 0.2, 0.24, or 0.32 mM, and aerobic culture was performed with shaking at 33° C. The growth of bacterial cells was determined by absorbance measurement at $OD_{610}$.

*Escherichia coli* JM109 was applied to LB agar medium (1% polypeptone, 0.5% yeast extract, 0.5% NaCl and 1.5% agar) and was left stand in the dark at 37° C. for 15 hours.

An inoculation loop of the *Escherichia coli* JM109 grown on a plate as above was inoculated into a test tube containing 10 mL of LB liquid medium (1% polypeptone, 0.5% yeast extract, and 0.5% NaCl), and aerobic culture was performed with shaking at 37° C. for 13 hours.

The *Escherichia coli* JM109 grown in the above conditions was inoculated into 100 mL of LB liquid medium in such a way that the initial bacterial cell concentration would be $OD_{610}$=0.05, phenol was added at the same time in such a way that the final concentration would be 0, 0.16, or 0.20 mM, and aerobic culture was performed with shaking at 37° C. The growth of bacterial cells was determined by absorbance measurement at $OD_{610}$.

*Pseudomonas putida* F1 and S12 were applied to LB agar medium (1% polypeptone, 0.5% yeast extract, 0.5% NaCl and 1.5% agar) and were left stand in the dark at 30° C. for 15 hours.

An inoculation loop of each of the *Pseudomonas putida* F1 and S12 grown on a plate as above was inoculated into a test tube containing 10 mL of LB (+glucose) liquid medium (1% polypeptone, 0.5% yeast extract, 0.5% NaCl and 0.4% glucose), and aerobic culture was performed with shaking at 30° C. for 13 hours.

Figure 2:
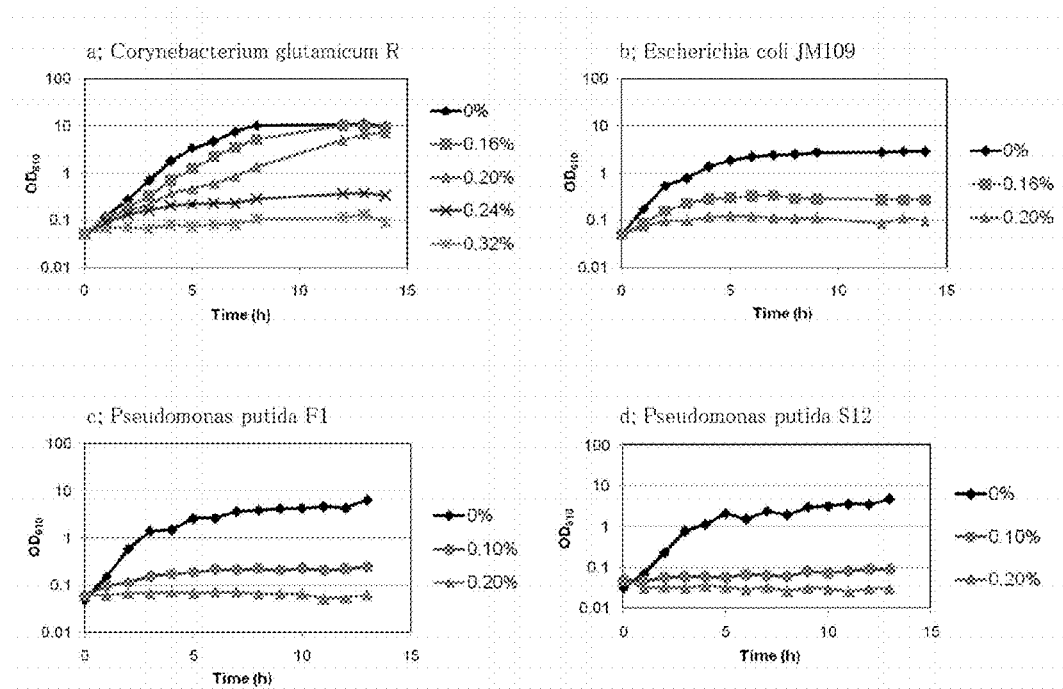
FIG. 2 shows the influence of phenol on proliferation of various microorganisms under aerobic conditions.

The *Pseudomonas putida* F1 and S12 grown in the above conditions were each inoculated into 100 mL of LB (+glucose) liquid medium in such a way that the initial bacterial cell concentration would be $OD_{610}$=0.05, phenol was added at the same time in such a way that the final concentration would be 0, 0.10, or 0.20 mM, and aerobic culture was performed with shaking at 30° C. The growth of bacterial cells was determined by absorbance measurement at $OD_{610}$. FIG. 2 shows analysis results of the influence of phenol addition on aerobic proliferation.

The proliferation of *Escherichia coli* was significantly affected by 0.16% phenol and completely inhibited by 0.20% phenol.

*Pseudomonas putida* F1, and *Pseudomonas putida* S12, which was reported as a solvent-resistant strain, showed a similar tendency, and the proliferation thereof was significantly affected by 0.10% phenol and completely inhibited by 0.20% phenol.

In contrast, the proliferation of *Corynebacterium glutamicum* was hardly affected by 0.16% phenol, which significantly affected the proliferation of *Escherichia coli*. Even in the presence of 0.20% phenol, which completely inhibited the proliferation of *Escherichia coli* and *Pseudomonas putida*, *Corynebacterium glutamicum* showed favorable growth. Further, *Corynebacterium glutamicum* was able to proliferate in the presence of 0.24% phenol.

Thus, it was shown that *Corynebacterium glutamicum* has a higher resistance to phenol as compared with *Escherichia coli* and *Pseudomonas putida*, and is highly suitable as a host in phenol production.

INDUSTRIAL APPLICABILITY

According to the process of the present invention, phenol can be produced from tyrosine with a practical efficiency using microorganisms.

The invention claimed is:

1. A phenol-producing transformant constructed by transferring a gene which encodes an enzyme having tyrosine phenol-lyase activity into a *Corynebacterium glutamicum* as a host.

2. The transformant of claim 1, wherein the gene which encodes an enzyme having tyrosine phenol-lyase activity is a gene derived from *Pantoea agglomerans*, a gene derived from *Citrobacter braakii*, a gene derived from *Desulfitobacterium hafniense*, a gene derived from *Chloroflexus aurantiacus*, a gene derived from *Nostoc punctiforme*, or a gene derived from *Treponema denticola*.

3. The transformant of claim 1, wherein the gene which encodes an enzyme having tyrosine phenol-lyase activity is the DNA of the following (a) or (b),
   (a) a DNA consisting of the base sequence of SEQ ID NO: 16, a DNA consisting of the base sequence of SEQ ID NO: 23, a DNA consisting of the base sequence of SEQ ID NO: 24, a DNA consisting of the base sequence of SEQ ID NO: 25, a DNA consisting of the base sequence of SEQ ID NO: 26, or a DNA consisting of the base sequence of SEQ ID NO: 27
   (b) a DNA which hybridizes to a DNA consisting of a complementary base sequence of any of the DNAs of (a) under stringent conditions and which encodes a polypeptide having tyrosine phenol-lyase activity, wherein the stringent conditions are conditions where hybridization occurs at a temperature 10° C. below the melting temperature (Tm) of a perfect hybrid.

4. The transformant of claim 1, wherein the *Corynebacterium glutamicum* as the host is a *Corynebacterium glutamicum* in which a gene which encodes an enzyme having phenol 2-monooxygenase activity on the chromosome is disrupted or deleted.

5. The transformant of claim 1, wherein the *Corynebacterium glutamicum* as the host is *Corynebacterium glutamicum* R (FERM BP-18976), ATCC13032, or ATCC13869.

6. The transformant of claim 1, wherein the *Corynebacterium glutamicum* as the host is a strain of *Corynebacterium glutamicum* R (FERM BP-18976), ATCC13032, or ATCC13869 in which a gene which encodes an enzyme having phenol 2-monooxygenase activity on the chromosome is disrupted or deleted.

7. A *Corynebacterium glutamicum* transformant PHE31 (Accession Number: NITE BP-999).

8. A process for producing phenol, which comprises a step of allowing the transformant of claim 1 to react in a reaction mixture containing tyrosine, a salt thereof, or an ester thereof under reducing conditions, and a step of collecting phenol from the reaction mixture.

9. The process of claim 8, wherein the transformant does not proliferate in the reaction step.

10. The process of claim 8, wherein the oxidation-reduction potential of the reaction mixture under reducing conditions is −200 mV to −500 mV.

* * * * *

SEQUENCE LISTING

<160> NUMBER OF SEQ ID NOS: 27

<210> SEQ ID NO 1
<211> LENGTH: 1195
<212> TYPE: DNA
<213> ORGANISM: Artificial sequence
<220> FEATURE:
<223> OTHER INFORMATION: pCASE1-ori

<400> SEQUENCE: 1

| | | |
|---|---|---|
| atgaaaaccg accgtgcacg ctcgtgtgag aaagtcagct acatgagacc aactacccgc | 60 |
| cctgagggac gctttgagca gctgtggctg ccgctgtggc cattggcaag cgatgacctc | 120 |
| cgtgagggca tttaccgcac ctcacggaag aacgcgctgg ataagcgcta cgtcgaagcc | 180 |
| aatcccgacg cgctctctaa cctcctggtc gttgacatcg accaggagga cgcgcttttg | 240 |
| cgctcttttgt gggacaggga ggactggaga cctaacgcgg tggttgaaaa ccccttaaac | 300 |
| gggcacgcac acgctgtctg ggcgctcgcg gagccattta cccgcaccga atacgccaaa | 360 |
| cgcaagcctt tggcctatgc cgcggctgtc accgaaggcc tacggcgctc tgtcgatggc | 420 |
| gatagcggat actccgggct gatcaccaaa accccgagc acactgcatg ggatagtcac | 480 |
| tggatcaccg ataagctgta tacgctcgat gagctgcgct tttggctcga agaaaccggc | 540 |
| tttatgccgc ctgcgtcctg gaggaaaacg cggcggttct cgccagttgg tctaggtcgt | 600 |
| aattgcgcac tctttgaaag cgcacgtacg tgggcatatc gggaggtcag aaagcatttt | 660 |
| ggagacgctg acggcctagg ccgcgcaatc caaaccaccg cgcaagcact taaccaagag | 720 |
| ctgtttgatg aaccactacc tgtggccgaa gttgactgta ttgccaggtc aatccataaa | 780 |
| tggatcatca ccaagtcacg catgtgggaca gacggcgccg ccgtctacga cgccacattc | 840 |
| accgcaatgc aatccgcacg cggaagaaa ggctggcaac gaagcgctga ggtgcgtcgt | 900 |
| gaggctggac atactctttg gaggaacatt ggctaaggtt tatgcacgtt atccacgcaa | 960 |
| cggaaaaaca gcccgcgagc tggcagaacg tgccggtatg tcggtgagaa cagctcaacg | 1020 |
| atggacttcc gaaccgcgtg aagtgttcat taaacgtgcc aacgagaagc gtgctcgcgt | 1080 |
| ccaggagctg cgcgccaaag gtctgtccat gcgcgctatc gcggcagaga ttggttgctc | 1140 |
| ggtgggcacg gttcaccgct acgtcaaaga agttgaagag aagaaaaccg cgtaa | 1195 |

<210> SEQ ID NO 2
<211> LENGTH: 2675
<212> TYPE: DNA
<213> ORGANISM: Artificial sequence
<220> FEATURE:
<223> OTHER INFORMATION: pHSG298

<400> SEQUENCE: 2

| | | |
|---|---|---|
| gaggtctgcc tcgtgaagaa ggtgttgctg actcatacca ggcctgaatc gccccatcat | 60 |
| ccagccagaa agtgagggag ccacggttga tgagagcttt gttgtaggtg gaccagttgg | 120 |
| tgattttgaa cttttgcttt gccacggaac ggtctgcgtt gtcgggaaga tgcgtgatct | 180 |
| gatccttcaa ctcagcaaaa gttcgattta ttcaacaaag ccacgttgtg tctcaaaatc | 240 |
| tctgatgtta cattgcacaa gataaaaata tatcatcatg aacataaaa ctgtctgctt | 300 |
| acataaacag taatacaagg ggtgttatga gccatattca acgggaaacg tcttgctcga | 360 |
| agccgcgatt aaattccaac atggatgctg atttatatgg gtataaatgg gctcgcgata | 420 |
| atgtcgggca atcaggtgcg acaatctatc gattgtatgg gaagcccgat gcgccagagt | 480 |
| tgtttctgaa acatggcaaa ggtagcgttg ccaatgatgt tacagatgag atggtcagac | 540 |

```
taaactggct gacggaattt atgcctcttc cgaccatcaa gcattttatc cgtactcctg    600
atgatgcatg gttactcacc actgcgatcc ccgggaaaac agcattccag gtattagaag    660
aatatcctga ttcaggtgaa aatattgttg atgcgctggc agtgttcctg cgccggttgc    720
attcgattcc tgtttgtaat tgtccttttt acagcgatcg cgtatttcgt ctcgctcagg    780
cgcaatcacg aatgaataac ggtttggttg atgcgagtga ttttgatgac gagcgtaatg    840
gctggcctgt tgaacaagtc tggaaagaaa tgcataagct tttgccattc tcaccggatt    900
cagtcgtcac tcatggtgat tctcacttg ataaccttat ttttgacgag ggaaattaa     960 taggttgtat tgatgttgga cgagtcggaa tcgcagaccg ataccaggat cttgccatcc    1020
tatggaactg cctcggtgag ttttctcctt cattacagaa acggcttttt caaaaatatg    1080
gtattgataa tcctgatatg aataaattgc agtttcattt gatgctcgat gagttttct    1140 aatcagaatt ggttaattgg ttgtaacact ggcagagcat tacgctgact tgacgggacg    1200
gcggctttgt tgaataaatc gcattcgcca ttcaggctgc gcaactgttg ggaagggcga    1260
tcggtgcggg cctcttcgct attacgccag ctggcgaaag gggatgtgc tgcaaggcga    1320 ttaagttggg taacgccagg gttttcccag tcacgacgtt gtaaaacgac ggccagtgcc    1380
aagcttgcat gcctgcaggt cgactctaga ggatccccgg gtaccgagct cgaattcgta    1440
atcatgtcat agctgtttcc tgtgtgaaat tgttatccgc tcacaattcc acacaacata    1500
cgagccggaa gcataaagtg taaagcctgg ggtgcctaat gagtgagcta actcacatta    1560
attgcgttgc gctcactgcc cgctttccag tcgggaaacc tgtcgtgcca gctgcattaa    1620
tgaatcggcc aacgcgcggg gagaggcggt ttgcgtattg gcgaactttt gctgagttga    1680
aggatcagat cacgcatctt cccgacaacg cagaccgttc cgtggcaaag caaaagttca    1740
aaatcagtaa ccgtcagtgc cgataagttc aaagttaaac ctggtgttga taccaacatt    1800
gaaacgctga tcgaaaacgc gctgaaaaac gctgctgaat gtgcgagctt cttccgcttc    1860
ctcgctcact gactcgctgc gctcggtcgt tcggctgcgg cgagcggtat cagctcactc    1920
aaaggcggta atacggttat ccacagaatc aggggataac gcaggaaaga acatgtgagc    1980
aaaaggccag caaaaggcca ggaaccgtaa aaaggccgcg ttgctggcgt ttttccatag    2040
gctccgcccc cctgacgagc atcacaaaaa tcgacgctca agtcagaggt ggcgaaaccc    2100
gacaggacta taaagatacc aggcgtttcc ccctggaagc tccctcgtgc gctctcctgt    2160
tccgaccctg ccgcttaccg gatacctgtc cgcctttctc ccttcgggaa gcgtggcgct    2220
ttctcaatgc tcacgctgta ggtatctcag ttcggtgtag tcgttcgct ccaagctggg    2280 ctgtgtgcac gaaccccccg ttcagcccga ccgctgcgcc ttatccggta actatcgtct    2340
tgagtccaac ccggtaagac acgacttatc gccactggca gcagccactg gtaacaggat    2400
tagcagagcg aggtatgtag gcggtgctac agagttcttg aagtggtggc ctaactacgg    2460
ctacactaga aggacagtat ttggtatctg cgctctgctg aagccagtta ccttcggaaa    2520
aagagttggt agctcttgat ccggcaaaca aaccaccgct ggtagcggtg gtttttttgt    2580
ttgcaagcag cagattacgc gcagaaaaaa aggatctcaa gaagatcctt tgatcttttc    2640 tacgggtct gacgctcagt ggaacgatcc gtcga                              2675
```

<210> SEQ ID NO 3
<211> LENGTH: 25
<212> TYPE: DNA
<213> ORGANISM: Artificial sequence
<220> FEATURE:
<223> OTHER INFORMATION: PCR primer

<400> SEQUENCE: 3
atagatctag aacgtccgta ggagc    25

<210> SEQ ID NO 4
<211> LENGTH: 26
<212> TYPE: DNA
<213> ORGANISM: Artificial sequence
<220> FEATURE:
<223> OTHER INFORMATION: PCR primer

<400> SEQUENCE: 4
atagatctga cttggttacg atggac    26

<210> SEQ ID NO 5
<211> LENGTH: 27
<212> TYPE: DNA
<213> ORGANISM: Artificial sequence
<220> FEATURE:
<223> OTHER INFORMATION: PCR primer

<400> SEQUENCE: 5
atagatctag gtttcccgac tggaaag    27

<210> SEQ ID NO 6
<211> LENGTH: 28
<212> TYPE: DNA
<213> ORGANISM: Artificial sequence
<220> FEATURE:
<223> OTHER INFORMATION: PCR primer

<400> SEQUENCE: 6
atagatctcg tgccagctgc attaatga    28

<210> SEQ ID NO 7
<211> LENGTH: 551
<212> TYPE: DNA
<213> ORGANISM: Corynebacterium glutamicum

<400> SEQUENCE: 7
ccgaagatct gaagattcct gatacaaatt ctgttgtgac ggaagatttg ttggaagaaa     60
tctagtcgct cgtctcataa aaacgaccga gcctattggg attaccattg aagccagtgt    120
gagttgcatc acactggctt caaatctgag actttacttt gtggattcac ggggggtgtag   180
tgcaattcat aattagcccc attcggggga gcagatcgcg gcgcgaacga tttcaggttc    240
gttccctgca aaactatttt agcgcaagtg ttggaaatgc ccccgtctgg ggtcaatgtc    300
tattttgaaa tgtgtttgta tgattttgaa tccgctgcaa atctttgtt tccccgctaa     360
agttggggac aggttgacac ggagttgact cgacgaatta ccaatgtga gtaggtttgg    420
tgcgtgagtt ggaaaatttc gccatactcg cccttgggtt ctgtcagctc aagaattctt    480
gagtgaccga tgctctgatt gacctaactg cttgacacat tgcatttcct acaatcttta    540
gaggagacac a                                                          551

<210> SEQ ID NO 8
<211> LENGTH: 425
<212> TYPE: DNA
<213> ORGANISM: Artificial sequence
<220> FEATURE:
<223> OTHER INFORMATION: rrnBT1T2 terminator

```
<400> SEQUENCE: 8
ctgttttggc ggatgagaga agattttcag cctgatacag attaaatcag aacgcagaag    60
cggtctgata aaacagaatt tgcctggcgg cagtagcgcg gtggtcccac ctgaccccat   120
gccgaactca gaagtgaaac gccgtagcgc cgatggtagt gtggggtctc cccatgcgag   180
agtagggaac tgccaggcat caaataaaac gaaaggctca gtcgaaagac tgggcctttc   240
gttttatctg ttgtttgtcg gtgaacgctc tcctgagtag gacaaatccg ccggagcgg    300 atttgaacgt tgcgaagcaa cggcccggag ggtggcgggc aggacgcccg ccataaactg   360
ccaggcatca aattaagcag aaggccatcc tgacggatgg ccttttttgcg tttctacaaa  420 ctctt                                                               425

<210> SEQ ID NO 9
<211> LENGTH: 31
<212> TYPE: DNA
<213> ORGANISM: Artificial sequence
<220> FEATURE:
<223> OTHER INFORMATION: PCR primer

<400> SEQUENCE: 9
ctctgtcgac ccgaagatct gaagattcct g                                   31

<210> SEQ ID NO 10
<211> LENGTH: 46
<212> TYPE: DNA
<213> ORGANISM: Artificial sequence
<220> FEATURE:
<223> OTHER INFORMATION: PCR primer

<400> SEQUENCE: 10
ctctgtcgac ggatccccat ggtgtgtctc tctaaagat tgtagg                    46

<210> SEQ ID NO 11
<211> LENGTH: 36
<212> TYPE: DNA
<213> ORGANISM: Artificial sequence
<220> FEATURE:
<223> OTHER INFORMATION: PCR primer

<400> SEQUENCE: 11
ctctgcatgc ccatggctgt tttggcggat gagaga                              36

<210> SEQ ID NO 12
<211> LENGTH: 41
<212> TYPE: DNA
<213> ORGANISM: Artificial sequence
<220> FEATURE:
<223> OTHER INFORMATION: PCR primer

<400> SEQUENCE: 12
ctctgcatgc tcatgaaaga gtttgtagaa acgcaaaaag g                        41

<210> SEQ ID NO 13
<211> LENGTH: 5118
<212> TYPE: DNA
<213> ORGANISM: Artificial sequence
<220> FEATURE:
<223> OTHER INFORMATION: pCRB207

<400> SEQUENCE: 13
agatctaggt ttcccgactg gaaagcgggc agtgagcgca acgcaattaa tgtgagttag    60
ctcactcatt aggcacccca ggctttacac tttatgcttc cggctcgtat gttgtgtgga   120
```

| | |
|---|---|
| attgtgagcg gataacaatt tcacacagga aacagctatg accatgatta cgaattcgag | 180 |
| ctcggtaccc ggggatcctc tagagtcgac ccgaagatct gaagattcct gatacaaatt | 240 |
| ctgttgtgac ggaagatttg ttggaagaaa tctagtcgct cgtctcataa aaacgaccga | 300 |
| gcctattggg attaccattg aagccagtgt gagttgcatc acactggctt caaatctgag | 360 |
| actttacttt gtggattcac ggggtgtag tgcaattcat aattagcccc attcggggga | 420 |
| gcagatcgcg gcgcgaacga tttcaggttc gttccctgca aaactatttt agcgcaagtg | 480 |
| ttggaaatgc ccccgtctgg ggtcaatgtc tattttgaa tgtgtttgta tgattttgaa | 540 |
| tccgctgcaa aatctttgtt tccccgctaa agttggggac aggttgacac ggagttgact | 600 |
| cgacgaatta tccaatgtga gtaggtttgg tgcgtgagtt ggaaaatttc gccatactcg | 660 |
| cccttgggtt ctgtcagctc aagaattctt gagtgaccga tgctctgatt gacctaactg | 720 |
| cttgacacat tgcatttcct acaatcttta gaggagacac accatggctg ttttggcgga | 780 |
| tgagagaaga ttttcagcct gatacagatt aaatcagaac gcagaagcgg tctgataaaa | 840 |
| cagaatttgc ctggcggcag tagcgcggtg gtcccacctg accccatgcc gaactcagaa | 900 |
| gtgaaacgcc gtagcgccga tggtagtgtg gggtctcccc atgcgagagt agggaactgc | 960 |
| caggcatcaa ataaaacgaa aggctcagtc gaaagactgg gcctttcgtt ttatctgttg | 1020 |
| tttgtcggtg aacgctctcc tgagtaggac aaatccgccg ggagcggatt tgaacgttgc | 1080 |
| gaagcaacgg cccggagggt ggcgggcagg acgcccgcca taaactgcca ggcatcaaat | 1140 |
| taagcagaag gccatcctga cggatggcct ttttgcgttt ctacaaactc tttcatgggg | 1200 |
| atccgtcgac ctgcaggcat gcaagcttgg cactggccgt cgttttacaa cgtcgtgact | 1260 |
| gggaaaaccc tggcgttacc caacttaatc gccttgcagc acatccccct tcgccagct | 1320 |
| ggcgtaatag cgaagaggcc cgcaccgatc gcccttccca acagttgcgc agcctgaatg | 1380 |
| gcgaatgcga tttattcaac aaagccgccg tcccgtcaag tcagcgtaat gctctgccag | 1440 |
| tgttacaacc aattaaccaa ttctgattag aaaaactcat cgagcatcaa atgaaactgc | 1500 |
| aatttattca tatcaggatt atcaatacca tatttttgaa aaagccgttt ctgtaatgaa | 1560 |
| ggagaaaact caccgaggca gttccatagg atggcaagat cctggtatcg gtctgcgatt | 1620 |
| ccgactcgtc aacatcaat acaacctatt aatttcccct cgtcaaaaat aaggttatca | 1680 |
| agtgagaaat caccatgagt gacgactgaa tccggtgaga atggcaaaag cttatgcatt | 1740 |
| tctttccaga cttgttcaac aggccagcca ttacgctcgt catcaaaatc actcgcatca | 1800 |
| accaaaccgt tattcattcg tgattgcgcc tgagcgagac gaaatacgcg atcgctgtta | 1860 |
| aaaggacaat tacaaacagg aatcgaatgc aaccggcgca ggaacactgc cagcgcatca | 1920 |
| acaatatttt cacctgaatc aggatattct tctaatacct ggaatgctgt ttcccgggg | 1980 |
| atcgcagtgg tgagtaacca tgcatcatca ggagtacgga taaaatgctt gatggtcgga | 2040 |
| agaggcataa attccgtcag ccagtttagt ctgaccatct catctgtaac atcattggca | 2100 |
| acgctacctt tgccatgttt cagaaacaac tctggcgcat cgggcttccc atacaatcga | 2160 |
| tagattgtcg cacctgattg cccgacatta tcgcgagccc atttataccc atataaatca | 2220 |
| gcatccatgt tggaatttaa tcgcggcttc gagcaagacg tttcccgttg aatatggctc | 2280 |
| ataacacccc ttgtattact gtttatgtaa gcagacagtt ttattgttca tgatgatata | 2340 |
| tttttatctt gtgcaatgta acatcagaga ttttgagaca caacgtggct tgttgaata | 2400 |
| aatcgaactt ttgctgagtt gaaggatcag atcacgcatc ttcccgacaa cgcagaccgt | 2460 |
| tccgtggcaa agcaaaagtt caaaatcacc aactggtcca cctacaacaa agctctcatc | 2520 |

```
aaccgtggct ccctcacttt ctggctggat gatggggcga ttcaggcctg gtatgagtca   2580
gcaacacctt cttcacgagg cagacctctc gacggagttc cactgagcgt cagacccgt   2640 agaaaagatc aaaggatctt cttgagatcc ttttttttctg cgcgtaatct gctgcttgca  2700
aacaaaaaaa ccaccgctac cagcggtggt ttgtttgccg gatcaagagc taccaactct  2760
ttttccgaag gtaactggct tcagcagagc gcagatacca aatactgttc ttctagtgta  2820
gccgtagtta ggccaccact tcaagaactc tgtagcaccg cctacatacc tcgctctgct  2880
aatcctgtta ccagtggctg ctgccagtgg cgataagtcg tgtcttaccg ggttggactc  2940
aagacgatag ttaccggata aggcgcagcg gtcgggctga acggggggtt cgtgcacaca  3000
gcccagcttg gagcgaacga cctacaccga actgagatac ctacagcgtg agctatgaga  3060
aagcgccacg cttcccgaag ggagaaaggc ggacaggtat ccggtaagcg gcagggtcgg  3120
aacaggagag cgcacgaggg agcttccagg gggaaacgcc tggtatcttt atagtcctgt  3180
cgggtttcgc cacctctgac ttgagcgtcg attttgtga tgctcgtcag ggggggcggag  3240 cctatggaaa aacgccagca acgcggcctt tttacggttc ctggccttt gctggccttt  3300 tgctcacatg ttctttcctg cgttatcccc tgattctgtg gataaccgta ttaccgcctt  3360
tgagtgagct gataccgctc gccgcagccg aacgaccgag cgcagcgagt cagtgagcga  3420
ggaagcggaa gaagctcgca cattcagcag cgttttttcag cgcgttttcg atcaacgttt  3480
caatgttggt atcaacacca ggtttaactt tgaacttatc ggcactgacg gttactgatt  3540
ttgaactttt gctttgccac ggaacggtct gcgttgtcgg gaagatgcgt gatctgatcc  3600
ttcaactcag caaaagttcg ccaatacgca accgcctct ccccgcgcgt tggccgattc  3660
attaatgcag ctggcacgag atctgacttg gttacgatgg actttgaaca cgccgagggt  3720
gactaaaccg ctggatttac gcggttttct tctcttcaac ttctttgacg tagcggtgaa  3780
ccgtgcccac cgagcaacca atctctgccg cgatagcgcg catggacaga cctttggcgc  3840
gcagctcctg gacgcgagca cgcttctcgt tggcacgttt aatgaacact tcacgcggtt  3900
cggaagtcca tcgttgagct gttctcaccg acataccggc acgttctgcc agctcgcggg  3960
ctgtttttcc gttgcgtgga taacgtgcat aaaccttagc caatgttcct ccaaagagta  4020
tgtccagcct cacgacgcac ctcagcgctt cgttgccagc cttttcttccc gcgtgcggat  4080 tgcattgcgg tgaatgtggc gtcgtagacg gcggcgccgt ctgtccacat gcgtgacttg  4140
gtgatgatcc atttatggat tgacctggca atacagtcaa cttcggccac aggtagtggt  4200
tcatcaaaca gctcttggtt aagtgcttgc gcggtggttt ggattgcgcg gcctaggccg  4260
tcagcgtctc caaaatgctt tctgacctcc cgatatgccc acgtacgtgc gctttcaaag  4320
agtgcgcaat tacgacctag accaactggc gagaaccgcc gcgttttcct ccaggacgca  4380
ggcggcataa agccggtttc ttcgagccaa aagcgcagct catcgagcgt atacagctta  4440
tcggtgatcc agtgactatc ccatgcagtg tgctcgggt ttttggtgat cagcccggag  4500
tatccgctat cgccatcgac agagcgccgt aggccttcgg tgacagccgc ggcataggcc  4560
aaaggcttgc gtttggcgta ttcggtgcgg gtaaatggct ccgcgagcgc ccagacagcg  4620
tgtgcgtgcc cgtttaaggg gttttcaacc accgcgttag gtctccagtc ctccctgtcc  4680
cacaaagagc gcaaaagcgc gtcctcctgg tcgatgtcaa cgaccaggag gttagagagc  4740
gcgtcgggat tggcttcgac gtagcgctta ccagcgcgt tcttccgtga ggtgcggtaa  4800
atgccctcac ggaggtcatc gcttgccaat ggccacagcg gcagccacag ctgctcaaag  4860
cgtccctcag ggcgggtagt tggtctcatg tagctgactt tctcacacga gcgtgcacgg  4920
```

```
tcggttttca ttcataatac gacatttaac caagtcagat gtttccccgg tttccggggg    4980
ttcccctgaa gaaccctttcc agtgcgagcg aagcgagctc cttttggccgg cgcccctcag    5040 gtagccctct aaggctccca gggctccgcc cctccctgag gttggctcaa gcctcctggt    5100
ggctcctacg gacgttct                                                   5118

<210> SEQ ID NO 14
<211> LENGTH: 29
<212> TYPE: DNA
<213> ORGANISM: Artificial sequence
<220> FEATURE:
<223> OTHER INFORMATION: PCR primer

<400> SEQUENCE: 14
ctctcatatg ctgttttggc ggatgagag                                         29

<210> SEQ ID NO 15
<211> LENGTH: 33
<212> TYPE: DNA
<213> ORGANISM: Artificial sequence
<220> FEATURE:
<223> OTHER INFORMATION: PCR primer

<400> SEQUENCE: 15
ctctcatatg gtgtctcctc taaagattgt agg                                    33

<210> SEQ ID NO 16
<211> LENGTH: 1371
<212> TYPE: DNA
<213> ORGANISM: Pantoea agglomerans

<400> SEQUENCE: 16
atgaactatc ctgccgagcc tttccgcatt aaaagtgttg aaaccgtatc aatgatctca     60
cgcgatgagc gtgttaaaaa aatgcaagaa gcgggctata acacgttttt actgaattca    120
aaggatatct acatcgatct gctgacagac agcggtacaa atgccatgag tgacaagcag    180
tgggcaggga tgatgattgg tgatgaagcc tacgcaggca gtgaaaactt ctaccatctc    240
gaaaaaacgg tgaaagagtt gtttggttc aaacacatcg ttccaaccca ccagggacgc    300
ggggcggaaa acctgctctc gcagctggcc attaagcccg gtcaatatgt cgcaggaaat    360
atgtacttta caacaacccg cttccatcag gaaaaaaatg gcgcaacctt tgtggatatt    420
gtccgcgatg aagcacatga cgccagcctg aatctcccct ttaaaggtaa tattgacctg    480 aataaaattag cgacgctcat taaagaaaaa ggcgccgaga acatcgccta tctctgcctt    540
gcggtcaccg tgaatctggc gggtgggcag cctgtttcaa tggcgaatat gcgtgccgta    600
catgaaatgg ccagcacgta tggcattaag atctattacg atgctacccg ttgcgttgaa    660 aatgccctatt ttatcaaaga gcaggaggcg ggctacgaga acgtcagtat caaagatatc    720
gtgcatgaaa tgttcagcta tgccgatggg tgcaccatga gcgtaaaaaa agattgtctg    780
gtgaatatcg gcggcttctt gtgtatgaac gatgaggaga tgttctcagc ggcaaaagag    840
ttggttgtcg tttatgaagg tatgccgtca tacggcgggc tggccggtcg ggatatggaa    900
gcaatggcta tttgggctacg tgaagccatg cagtatgaat atattgaaca tcgggtcaaa    960
caggtgcgct atctgggcga taaactccgt gaagccggcg tacccattgt tgaaccgacg   1020
ggcggacatg cggtatttct tgatgctcgt cgtttctgtc cacacctgac gcaggatcag   1080
ttccctgcgc agagcctggc agccagcatc tatatgaaaa ccggcgtgcg aagtatgaaa   1140
cgtggaattg tttccgccgg tcgtagcaag gaaacggggg agaaccatag ccccaaactg   1200
```

```
gagacggtac gtctcactat tccacgccgt gtttacactt acgcgcacat ggatgttatt    1260
gccgatggca tcattaaact gtaccagcat aaagaagata ttcgtggtct gacgtttgtt    1320
tacgaaccta acaacttcg cttctttact gcgcgttttg actttattta a              1371
```

<210> SEQ ID NO 17
<211> LENGTH: 26
<212> TYPE: DNA
<213> ORGANISM: Artificial sequence
<220> FEATURE:
<223> OTHER INFORMATION: PCR primer
<400> SEQUENCE: 17

```
ctctcatatg aactatcctg ccgagc                                          26
```

<210> SEQ ID NO 18
<211> LENGTH: 38
<212> TYPE: DNA
<213> ORGANISM: Artificial sequence
<220> FEATURE:
<223> OTHER INFORMATION: PCR primer
<400> SEQUENCE: 18

```
ctctcatatg ttaaataaag tcaaaacgcg cagtaaag                             38
```

<210> SEQ ID NO 19
<211> LENGTH: 29
<212> TYPE: DNA
<213> ORGANISM: Artificial sequence
<220> FEATURE:
<223> OTHER INFORMATION: PCR primer
<400> SEQUENCE: 19

```
ctcttctaga tacgtcctaa acacccgac                                       29
```

<210> SEQ ID NO 20
<211> LENGTH: 40
<212> TYPE: DNA
<213> ORGANISM: Artificial sequence
<220> FEATURE:
<223> OTHER INFORMATION: PCR primer
<400> SEQUENCE: 20

```
gaccaaccat tgctgacttg cgtatccata gtcaggcttc                           40
```

<210> SEQ ID NO 21
<211> LENGTH: 20
<212> TYPE: DNA
<213> ORGANISM: Artificial sequence
<220> FEATURE:
<223> OTHER INFORMATION: PCR primer
<400> SEQUENCE: 21

```
caagtcagca atggttggtc                                                 20
```

<210> SEQ ID NO 22
<211> LENGTH: 30
<212> TYPE: DNA
<213> ORGANISM: Artificial sequence
<220> FEATURE:
<223> OTHER INFORMATION: PCR primer
<400> SEQUENCE: 22

```
ctcttctaga tgatcagtac caagggtgag                                      30
```

<210> SEQ ID NO 23
<211> LENGTH: 1371
<212> TYPE: DNA
<213> ORGANISM: Citrobacter braakii

<400> SEQUENCE: 23

| | | | | | |
|---|---|---|---|---|---|
| atgaattatc | cggcagaacc | cttccgtatt | aaaagcgttg | aaactgtatc | tatgatcccg | 60 |
| cgtgatgaac | gccttaagaa | atgcaggaa | gcgggataca | atactttcct | gttaaattcg | 120 |
| aaagatattt | atattgacct | gctgacagac | agtggcacca | acgcaatgag | tgacaagcag | 180 |
| tgggccggca | tgatgatggg | tgatgaagcc | tacgcgggca | gcgaaaactt | ctatcatctg | 240 |
| gaaagaaccg | tgcaggaact | gttcggcttt | aaacatattg | ttcctactca | ccagggggcgc | 300 |
| ggcgcagaaa | acctgttatc | gcagctggca | attaaaccgg | gcaatatgt | tgccgggaat | 360 |
| atgtatttca | ctaccacccg | ttatcaccag | gaaaaaaatg | gtgcggtgtt | tgtcgatatc | 420 |
| gttcgtgatg | aagcgcacga | tgccggtctg | aatattgctt | ttaaaggtga | tatcgatctt | 480 |
| aaaaaattac | aaaagctgat | tgatgaaaaa | ggcgccgaga | atattgccta | tatttgcctg | 540 |
| gcagtcacgg | ttaacctcgc | aggcgggcag | ccggtctcca | tggctaacat | gcgcgcggtg | 600 |
| cgtgaactga | ctgcagcaca | tggcattaaa | gtgttctacg | acgctacccg | ctgcgtagaa | 660 |
| aacgcctact | ttatcaaaga | gcaagagcag | ggctttgaga | caagagcat | cgcagagatc | 720 |
| gtgcatgaga | tgttcagcta | cgccgacggt | tgtaccatga | gtggtaaaaa | agactgtctg | 780 |
| gtgaatatcg | gcggcttcct | gtgcatgaac | gatgacgaaa | tgttctcttc | tgccaaagag | 840 |
| ttagtcgttg | tttacgaagg | tatgccatct | tacggcggcc | tggccggacg | cgacatggaa | 900 |
| gccatggcga | ttggtctgcg | cgaagccatg | cagtatgagt | acatcgagca | ccgcgtgaag | 960 |
| caggttcgct | atctgggcga | caagctgaaa | gccgctggtg | taccgattgt | tgaaccggtg | 1020 |
| ggcggtcatg | cggtattcct | cgatgcgcgt | cgcttctgtg | agcatctgac | gcaggacgag | 1080 |
| ttcccggcgc | aaagcctggc | tgccagtatc | tatgtggaaa | ccggcgtacg | tagtatggag | 1140 |
| cgcggaatta | tctctgcggg | ccgtaataac | gtgaccggtg | aacaccacag | gccgaaactg | 1200 |
| gaaaccgtgc | gtctgactat | tccacgccgc | gtttatactt | acgcgcatat | ggatgtggtg | 1260 |
| gctgacggta | ttattaaact | ttaccagcac | aaagaagata | ttcgcgggct | gaagtttatt | 1320 |
| tacgagccga | agcagctccg | tttctttact | gcacgctttg | actatatcta | a | 1371 |

<210> SEQ ID NO 24
<211> LENGTH: 1374
<212> TYPE: DNA
<213> ORGANISM: Desulfitobacterium hafniense

<400> SEQUENCE: 24

| | | | | | |
|---|---|---|---|---|---|
| atgaaaacct | atcctgcaga | acctttaga | attaaagtcg | tggaacccgt | tcggtcgatg | 60 |
| aagcgggcag | aacgtgaagc | ggccatgaaa | gaagcaggct | acaacacttt | tttgctgaag | 120 |
| agtgaggatg | tctatattga | tctgctcaca | gattccggca | ctactgccat | gagcgataaa | 180 |
| caatgggccg | gtatgatgat | cggtgatgaa | gcctatgccg | ggagcaggaa | tttcctgcac | 240 |
| ctggatcggg | tggttaaaga | atattatggc | ttcaagcaca | tggtccctac | tcatcaagga | 300 |
| cggggggcgg | aaaacctgct | ctcccggctg | atgattaaac | ccggggatta | tgtgcccggc | 360 |
| aatatgtatt | ttaccaccac | aagataccat | caggaagcca | acggagctac | cttcagagat | 420 |
| attatcattg | tgaagcccca | tgactcagcc | aaccggcatc | ctttcaaagg | aaatatcgat | 480 |
| ctcaggaaac | tccagacctt | aatcgatgaa | gtaggcgcgg | agaagattcc | ttacatctgc | 540 |

| | |
|---|---|
| cttgccgtta ctgtcaatct ggccggagga cagcccgttt ctctggaaaa catgaaggcg | 600 |
| gtccatgagc ttgcccacaa acacggcatc aaggtgtttt ttgacgctac ccgctgtgtg | 660 |
| gagaacgctt acttcatcaa gaagcgggaa gcagactacc aggacaagac catcaaagaa | 720 |
| attctcttgg agatgatgag ctatgccgac ggagccacca tgtcgggtaa aaaagattgt | 780 |
| atggtcaata tcggcggttt tctggccatg aatgatgatg aattgttcct cagggttaaa | 840 |
| gaactggtgg tggtctttga aggaatgcct tcttacggcg gcatggccgg ccgggacatg | 900 |
| gaagccatgg ccatcgggat tacggaatcg gtggattatg cttatattga caccgtgtg | 960 |
| gagcaggtgg cctatcttgc cgatcagctt ttagcggcgg gggttcccat tgtggaaccg | 1020 |
| gtgggcggcc atgccgtctt ccttgatgcc agacggtttt tgccccacct tgagcaggac | 1080 |
| cacttcccgg cacaggctct ggccgcccaa ttatatatag aatccggggt acgtctctatg | 1140 |
| gaaagaggaa tcatctccgc cggacgtgat cttaaaacag gggaaaaccg ccatcctaaa | 1200 |
| ctggagctgg taaggctgac gattccccgc cgggtttata cttacgctca tatgggacatc | 1260 |
| gtggccagag cggttattga gctttaccag caaagggaga ccatcaaagg cttaaatttt | 1320 |
| gtttacgaac cggaaatgct tcgtttcttc accgccagat ttgaacacat ttga | 1374 |

<210> SEQ ID NO 25
<211> LENGTH: 1419
<212> TYPE: DNA
<213> ORGANISM: Chloroflexus aurantiacus

<400> SEQUENCE: 25

| | |
|---|---|
| atgcaggaac aagactaccc ccgtacaatg gggcaacaat tcggtcggcg gtcgtgggcc | 60 |
| gagccgtgga agatcaagat ggttgagccg ctgcgcgtga ccagccgggc cgaacgcgag | 120 |
| gcggcgctga aggctgccgg ttacaacacg tttctgctgc gttctgaaga tgtctatatc | 180 |
| gatctgctta ccgatagtgg taccaatgcc atgagcgacc ggcaatgggc agccctgatg | 240 |
| atgggcgacg aggcatacgc cgggagccgc agtttttatc gcctggaagc aactgtccaa | 300 |
| caggtgtatg gctaccgcca cattattccc acccatcagg ggcggggcgc cgagcatctg | 360 |
| atcagtcagg tcgctatccg ccgtgggcag tatgttcccg gcaatatgta tttcacaacc | 420 |
| acccgcctgc accaggagct ggccggtggc atctttgttg atgtgattat tgacgaagcg | 480 |
| cacgatcccc aaagccagta tccgtttaaa ggcaacgtcg atctcgacaa actacaggcg | 540 |
| ctgattgata aggttggccc gcaacagatt gcctatatca gtctggccgg taccgtcaac | 600 |
| atggctggtg gcagccggt cagtatggct aacgtccgtg ccttacgcgc attatgtgat | 660 |
| cggtacgggt gcgcatctt tctcgattcc acacgcttgg ttgagaatgc ctttttcatc | 720 |
| aaagaacgtg aacccggcta tgccgaacaa agaatcgccg cgattgtccg cgagttttgc | 780 |
| agttacaccg atggcgcatg gatgagcgca agaaggacg cgctggtgaa catcggtggc | 840 |
| tggttagcgc tcaacgatga tcaactcgcc gatgaagccc gcaatctggt ggtggtgtac | 900 |
| gaagggttgc acacctacgg cggcatggcc gggcgtgata tggaggcgct ggcggtcggg | 960 |
| attgaggagt cgctgcaaga ggattacatc cgtgcccgca tcggtcaggt gcgctacctc | 1020 |
| ggcgaactgc tcctcgactg gacatcccc atcgtagttc cgattggcgg tcacgcgatc | 1080 |
| tttctggatg cacgccggtt ctatccgcac ctgccgcaag acctcttccc tgcccagacc | 1140 |
| ctggccgccg agttgtacct cgattcaggg gtgcgggcta tggaacgcgg tattgccagc | 1200 |
| gccgacgcga tcccaagac cgggcagaac tactatccca aactggaatt aacccggctg | 1260 |
| accatcccgc gccgtgttta tactcaggcc cacatggatg ttgtggccga gtcggtgaag | 1320 |

| | |
|---|---|
| gcagtgtacg atcaacgtca tcaggcccgt ggcctgcgga tggtctacga accacggtac | 1380 |
| ctccgcttct tccaggcccg gtttgaaccg gtggaatga | 1419 |

<210> SEQ ID NO 26
<211> LENGTH: 1404
<212> TYPE: DNA
<213> ORGANISM: Nostoc punctiforme

<400> SEQUENCE: 26

| | |
|---|---|
| atgaccgatg ccaagcaaac ttctccgcgc cgccgtcgct cttgggcaga gccatataaa | 60 |
| attaaggtgg ttgagccatt aaaaattact actcgcgctg aacgcgaaca ggcgatcgca | 120 |
| caagcgggtt acaatacttt tctactacgt tctgaagatg tctatattga tttgctcact | 180 |
| gatagcggca cttcagccat gagcgattat cagtgggcag ggatgatgct gggtgatgaa | 240 |
| gcttatgccg gcagcaaaaa ttttttacaat ttagaagcaa gtatccaaaa gtattacggc | 300 |
| tatcgccata ttgtacctac tcaccaaggg cgtggtgcag aaaatattct ttctcaaata | 360 |
| ctgatcaaac caggagacta catacctggc aatatgtatt tcaccacaac caggttgcat | 420 |
| caggagttag ctgcggcac ttttgtcgat gtgattattg atgaagccca cgatgcccaa | 480 |
| tcactgcatc catttaaggg taatgtagac ttacaaaagc ttacagacct aattgagcga | 540 |
| gttggggcag aacgtattcc ctatattagc gttgccggaa ccgtgaatat ggctggcgga | 600 |
| cagccgattt ctatgctaa cctgcgggcg gtacatcagt tagcccaaac ctacggtatc | 660 |
| cgcattattc ttgatgccac ccgcgctgtg aaaacgctc actttatcca acagcgagag | 720 |
| gaggattatt ccagccaagc gatcgctacc atcttacgcg aattttgctc ctataccgac | 780 |
| ggttgcacca tgagcggtaa gaaggatgca ctggttaaca tcggcggttg gctggctctt | 840 |
| aatgactata tctttacga agaagcacgt aacttaatag taatttatga aggtctacat | 900 |
| acttacggtg gtatggctgg ccgggacatg gaagctatgg cacgaggtat agaagaatca | 960 |
| gttcaagacg atcatattcg tgcccgtgtc ggtcaggttg agtatcttgg acaaaagctt | 1020 |
| ttagattggg gtattccaat tgttgtgccg attggcggtc atgccattta tttagatgcc | 1080 |
| aaacgctttt taccacaaat tccccaagac caatttccgg cacaacgtct agcagcagaa | 1140 |
| ctgtatctag aggcaggcat tcgggcaatg gaacggggca tcgtttccgc agggcgcaat | 1200 |
| aaagaaacag gcgataatta ttatccagag ttagaattag tccgtttaac tattccacgc | 1260 |
| cgtgtttaca ctcaggctca catggatctg actgctgaag cagttgaaga gtttatcat | 1320 |
| aatcgcgatc gcctacgcgg actcaaaatg atttatgagc cgaagtatct ccgtttctttt | 1380 |
| caagcaagat ttgaattgca gtaa | 1404 |

<210> SEQ ID NO 27
<211> LENGTH: 1380
<212> TYPE: DNA
<213> ORGANISM: Treponema denticola

<400> SEQUENCE: 27

| | |
|---|---|
| atggatatta aaaattatcc tgcggaacct tttagaatta aggttgtaga aactgttaag | 60 |
| atgatcgata aggatcaaag agcaaaggtt gccaaagaag ccggttataa taccttcctt | 120 |
| attaattcgg aagatgttta tatcgacctt cttaccgact ccggaacaaa cgccatgagc | 180 |
| gataaacaat gggccggaat gatgatagga gatgaagcct atgccggaag ccgcaacttt | 240 |
| catcacttgg aagaaacggt tcaagagatt ttcggcttta agcatcttgt gccgacccat | 300 |
| caaggccgcg gtgccgaaaa ccttctttca aggatagcca ttaaaccccgg tcaatatgta | 360 |

```
cccggcaaca tgtattttac cactaccaga taccatcagg aagcaaacgg cggtatcttc    420
gtggatatca taaacgatga tgctcatgat gcaggcaaaa atgttccttt taaaggcgac    480
atcgacttga acaagcttga aaagcttata aaagaaaagg gagccgaaaa tatagcctat    540
gtatgtttgg ctgttacggt aaaccttgca ggcggtcagc ccgtttctat gaagaacatg    600
aaggccgtcc gtgagcttac aaaaaagcac ggcatcaagg tattctacga tgcaacccgc    660
tgtgtagaaa acgcctactt tatcaaagaa caagaagccg gttatgccga caagtctatc    720
aaagaaatcg taagagaaat gttcagctat gcagacggat gtaccatgag cggtaaaaaa    780
gactgtatcg taaacatcgg aggcttcctc tgtatgaacg atgaagatct tttccaagct    840
gcaaaagaat tcgttgttgt atttgaaggt atgccttcat acggcggtat ggcaggacgc    900
gatatggaag ctatggctat cggtctaaaa gaagctctcc agtttgaata catcgaacac    960
cgaatcaagc aggtccgcta tttaggcgac aagctcttgg aagccggagt tcctattatt   1020
gagcccgtag gaggacatgc agtatttctt gatgcaagac gcttctgtcc tcatcttaag   1080
caaaccgaat ttcccgcaca ggccctagcc gcagagcttt atatcgaatc gggagttaga   1140
agtatggaac gcggtatcgt ttctgcagga cgcgatccca aaacaaggga aaaccacgta   1200
ccaaagcttg aaacagtccg cttaacaatt ccgcgccgtg tttatacata taaacacatg   1260
gacattgtag cagatgccgt tattaaattg tacaaacaca aggaagttat aaaaggatta   1320
aagttcgttt acgaacctaa acaactccgc ttctttacgg cacgctttga gcatatctaa   1380
```